United States Patent
Lee et al.

(10) Patent No.: US 6,774,110 B2
(45) Date of Patent: Aug. 10, 2004

(54) ORALLY AVAILABLE PEPTIDIC THROMBIN INHIBITORS

(75) Inventors: Koo Lee, Taejon (KR); Cheol-Won Park, Taejon (KR); Won-Hyuk Jung, Taejon (KR); Sang-Koo Lee, Taejon (KR)

(73) Assignee: LG Life Sciences Ltd., Seoul (KR)

( * ) Notice: Subject to any disclaimer, the term of this patent is extended or adjusted under 35 U.S.C. 154(b) by 96 days.

(21) Appl. No.: 09/810,243

(22) Filed: Mar. 19, 2001

(65) Prior Publication Data

US 2002/0169113 A1 Nov. 14, 2002

(51) Int. Cl.[7] .................................................. C07K 5/06
(52) U.S. Cl. ............................... 514/19; 514/269; 546/1
(58) Field of Search ......................... 514/19, 269; 546/1

(56) References Cited

U.S. PATENT DOCUMENTS 6,288,077 B1 * 9/2001 De Nanteuil et al. ....... 514/299
6,444,817 B1 * 9/2002 Bohm et al. ................ 544/334

OTHER PUBLICATIONS

Lumma, J. Med. Chem. 41, 1011 1998.*

* cited by examiner

Primary Examiner—Robert A. Wax
Assistant Examiner—David Lukton
(74) Attorney, Agent, or Firm—Birch, Stewart, Kolasch & Birch, LLP

(57) ABSTRACT

The present invention relates to novel thrombin inhibitors that are useful as anticoagulants. More particularly, the present invention is directed to peptide derivatives having high antithrombotic activity and high oral bioavailability.

8 Claims, No Drawings

ORALLY AVAILABLE PEPTIDIC THROMBIN INHIBITORS

TECHNICAL FIELD OF THE INVENTION

The present invention relates to thrombin inhibitors that are useful as anticoagulants. In particular, the present invention is directed to peptide derivatives having high antithrombotic activity and high oral bioavailability as well.

BACKGROUND OF THE INVENTION

Thrombosis, excessive blood clotting, plays a significant role in cardiovascular and related diseases, and thrombotic events underlie a significant proportion of the mortality and morbidity associated with cardiovascular disease. This thrombosis causes a range of significant disease states which are characterized by the location of the blood vessel in which the clot is formed.

Thrombin is a trypsin-like serine protease that plays a key role in the blood coagulation cascade by catalyzing the conversion of fibrinogen to insoluble. This enzyme also activates factor V and factor VIII for its own production and potently activates platelets as well. Therefore, thrombin has long been recognized as a central regulator in thrombosis and hemostasis, and its inhibition has become a major therapeutic target in the treatment of cardiovascular diseases such as myocardial infarction, unstable angina, deep vein thrombosis and pulmonary embolism.

Indirect thrombin inhibitors such as heparin and warfarin (coumarin) have been used as antithrombotic therapies with, however, several limitations. Heparin demonstrates low bioavailability and is associated with side effects such as bleeding problems, moreover, it is not able to inhibit clot-bound thrombin. Warfarin is an effective oral anticoagulant but it has a narrow therapeutic window and also requires patient monitoring. A natural protein inhibitor, hirudin, has been associated with bleeding complications.

Most of low molecular weight thrombin inhibitors are broadly based upon peptides or peptidomimetic templates which operate by a direct mechanism of action against the target enzyme. Early examples are tripeptidic aldehydes such as D-Phe-Pro-Arg-H and Me-D-Phe-Pro-Arg-H that have been reported to be effective thrombin inhibitors (Bajusz et al. *J. Med. Chem.* 1990, 33, 1729).

Recently, D-Phe-Pro-Agmatine and its derivatives have been described as thrombin inhibitors in U.S. Pat. No. 4,346,078 and WO 93/11152 (agmatine: 1-amino-4-guanidinobutane). These compound are different from the earlier tripeptidic compounds in that the agimatine compounds lack a carbonyl moiety found in similar compounds containing an Arg side chain.

More recently, certain tripeptidic thrombin inhibitors in which 4-amidinobenzylamine is incorporated at P1 position in place of agmatine, have been disclosed (WO 94/29336, WO 95/23609, WO 96/17860, WO 96/24609, WO 96/25426). These amidine-based compounds possess in most cases mono-substituted D-alanine and D-glycine such as phenylalanine, cyclohexylalanine, and cyclohexylglycine. Good antithrombotic activity of this class of compounds is also reported (WO 95/23609).

Certain tripeptidic thrombin inhibitors bearing di-substituted D-alanine (i.e. D-diphenylalanine) at P3 position and non-amidine P1 moieties have been disclosed (WO 93/11152, U.S. Pat. No. 5,510,369, WO 97/15190). These compounds have been reported to have higher potency against thrombin compared to the corresponding mono-substitued D-alanine alalogs (i.e. D-phenylalanine) (*J. Med. Chem.* 1992, 35, 3365; *J. Med. Chem.* 1997, 40, 830). In addition, some of this class of compounds exhibited good oral bioavailability (*J. Med. Chem.* 1997, 40, 3687; *J. Med. Chem.* 1997, 40, 3726).

Very recently, certain tripeptidic thrombin inhibitors bearing both D-diphenylalanine at P3 position and 5-membered-aryl amidine (e.g. thienylamidine) at P1 side chain have been disclosed (WO 00/39124). This class of compounds exhibited high antithrombotic activity and high oral bioavailability as well.

Therefore, there is a need in the art for thrombin inhibitors which have improved oral bioavailability and stablility as compared to those described supra. The present inventors have found that the compounds of the present invention, as defined below, are potent inhibitors of thrombin in vitro and in vivo. In particular, the compounds of the present invention exhibit high bioavailability after oral administration.

SUMMARY OF THE INVENTION

It is an object of the present invention to provide compound of the following chemical formula (I) which modulate and/or inhibit the serine protease thrombin, as well as acceptable prodrugs, pharmaceutically active metabolites, and pharmaceutically acceptable salts thereof (hereinafter, such compounds, prodrugs, metabolites and salts are collectively referred to as "agents"). Other objects of the present invention are to provide pharmaceutical compositions containing the compound of formula (I) and to provide their therapeutic use in treating diseases mediated by thrombin, such as myocardial infarction, unstable angina, deep vein thrombosis and pulmonary embolism, as well as other disease states associated with blood clotting and associated clotting factors.

The above objects of the present invention are achieved by providing compound of the following chemical formula (I)

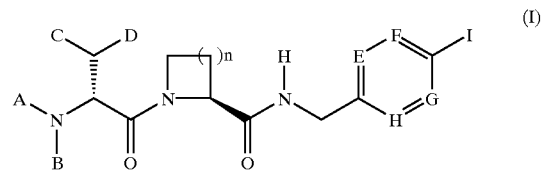

and pharmaceutically acceptable salts thereof
wherein
n is 1 or 2;
A is hydrogen, $C_{1-6}$ alkyl, aryl, $-SO_2R^1$, $-PO(OC_{1-6}$ alkyl$)_2$, $-PO(C_{1-6}$ alkyl$)_2$, $-CO(C_{1-6}$ alkyl), $-C_2R^2$, $-(CH_2)_mCO_2H$ or $-(CH_2)_mCO_2(C_{1-6}$ alkyl),
wherein
$R^1$ is hydrogen, $C_{1-6}$ alkyl, $C_{3-7}$ cycloalkyl, aryl, $-(CH_2)_m$aryl or $-NR3R^4$
$R^2$ is $C_{1-6}$ alkyl, $C_{3-7}$ cycloalkyl, aryl, $-(CH_2)_m$aryl or alkenyl, and
m is 1, 2 or 3,
wherein
aryl is unsubsituted, substituted phenyl or 5–6 membered aromatic heterocyclic ring, and
$R^3$ and $R^4$ are independently hydrogen, $C_{1-6}$ alkyl or $C_{3-7}$ cycloalkyl;
B is hydrogen;
C and D are both 'phenyl unsubsituted or substituted with one or two substituents selected from $C_{1-4}$ alkyl, $C_{1-4}$ alkoxy, methylenedioxy, halogen, hydroxy and $NR^4R^5$, or
$C_{3-7}$ cycloalkyl;

E, F, G, and H are independently $CR^5$ or N
 wherein
  $R^5$ is hydrogen, $C_{1-4}$ alkyl, $C_{1-4}$ alkoxy, $CF_3$, halogen, hydroxy or $-NR^4R^5$; and
 I is $-C(NH)NH_2$, $-C(NH_2)NOH$, or $-CH_2NH_2$.

Another object of the present invention is achieved by providing pharmaceutical compositions comprising: an effective amount of an agent selected from compounds of Formula (I) and pharmaceutically acceptable salts, pharmaceutically active metabolites, and pharmaceutically acceptable prodrugs thereof, and a pharmaceutically acceptable carrier or vehicle for such agent. The present invention further provides methods of treating cardiovascular diseases such as myocardial infarction, unstable angina, deep vein thrombosis and pulmonary embolism, as well as other disease states associated with excess thrombin.

The present invention is further explained in more detail hereinbelow.

DETAILED DESCRIPTION OF THE INVENTION

The present invention provide compounds of Formula (I) which are useful for mediating the activity of trypsin-like serine proteases. More particularly, the compounds of the present invention are useful as anti-coagulant agents and as agents for modulating and/or inhibiting the activity of trypsin-like serine proteases, thus providing treatments for thrombosis and other cardiovascular diseases such as myocardial infarction, unstable angina, deep vein thrombosis and pulmonary embolism.

The terms and abbreviations used in the instant disclosure have their normal meanings unless otherwise designated.

As used in the present invention, the following definitions apply:

Where chiral carbons are included in chemical structures, unless a particular orientation is depicted, both stereoisomeric forms are intended to be encompassed.

An "alkyl group" is intended to mean a straight or branched chain monovalent radical of saturated and/or unsaturated carbon atoms and hydrogen atoms, such as methyl (Me), ethyl (Et), propyl, isopropyl, butyl (Bu), isobutyl, t-butyl (t-Bu), ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable sustituents as defined below (e.g., one or more halogens, such as F, Cl, Br, or I, with F and Cl being preferred).

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents.

A "heterocycloalky group" is intended to mean a non-aromatic monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents.

An "aryl group" is intended to mean an aromatic monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl)., or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents.

A "heterocycle" is intended to mean a heteroaryl or heterocycloalkyl group (each of which, as defined above, are optionally substituted).

A "hydroxy group" is intended to mean the radical —OH.

An "amino group" is intended to mean the radical —$NH_2$.

An "alkoxy group" is intended to mean the radical —$OR_a$, where $R_a$ is an alkyl group. Exemplary alkoxy groups include methoxy, ethoxy, propoxy, and the like. group.

A "carboxy group" is intended to mean the radical —C(O)OH.

Typical protecting groups, reagents and solvents are well known in the art. One skilled in the art would know possible protecting groups, reagents and solvents; these are intended to be within the scope of this invention.

The term "substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

A "pharmaceutically acceptable prodrug" is a compound that may be converted under physiological conditions or by solvolysis to the specified compound or to a pharmaceutically acceptable salt of such compound.

A "pharmaceutically active metabolite" is intended to mean a pharmacologically active product produced through metabolism in the body of a specified compound or salt thereof. Metabolites of a compound may be identified using routine techniques known in the art and their activities determined using tests such as those descibed herein.

A "pharmaceutically acceptable salt" is intended to mean a salt that retains the biological effectiveness of the free acids and bases of the specified compound and that is not biologically or otherwise undesirable. The compound of the present invention may possess a sufficiently acidic, a sufficiently basic, or both functional groups, and accordingly react with any of a number of inorganic or organic bases, and inorganic and organic acids, to form pharmaceutically acceptable salt. Exemplary pharmaceutically acceptable salts include those salts prepared by reaction of the compounds of the present invention with a nimeral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, glycollates, tartrates, methane-sulfonates, propanesulfonates, naphthalene-1-sulfonates, naphthalene-2-sulfonates, and mandelates.

In case that the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In case that the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Preferred compounds of the present invention include, but are not limited to the following:

1. N-aminosulfonyl-D-diphenylalanyl-L-prolyl-[(4-amidinophenyl)methyl]amide,
2. N-aminosulfonyl-D-diphenylalanyl-L-prolyl-[(4-aminomethylphenyl)methyl]amide,
3. N-aminosulfonyl-D-dicyclohexylalanyl-L-prolyl-[(4-amidinophenyl)methyl]amide,
4. N-aminosulfonyl-D-diphenylalanyl-L-azetidine-2-carboxyl-[(4-amidinophenyl)methyl]amide,
5. N-Aminosulfonyl-D-valinyl-L-prolyl-[(4-amidinophenyl)methyl]amide,
6. N-aminosulfonyl-D-diphenylalanyl-L-prolyl-(6-amidino-3-picolyl)amide,
7. N-aminosulfonyl-D-diphenylalanyl-L-prolyl-(6-aminomethyl-3-picolyl)amide,
8. N-aminosulfonyl-D-dicyclohexylalanyl-L-prolyl-(6-amidino-3-picolyl) amide,
9. N-aminosulfonyl-D-diphenylalanyl-L-prolyl-(5-amidino-2-picolyl)amide,
10. N-aminosulfonyl-D-diphenylalanyl-L-prolyl-[(2-amidino-5-pyrimidyl)methyl]amide,
11. N-aminosulfonyl-D-diphenylalanyl-L-prolyl-[(4-amidino-3-fluorophenyl)methyl]amide,
12. N-aminosulfonyl-D-diphenylalanyl-L-prolyl-[(4-amidino-2-fluorophenyl)methyl]amide,
13. N-aminosulfonyl-D-diphenylalanyl-L-prolyl-[(4-amidino-3-methylphenyl)methyl]amide,
14. N-aminosulfonyl-D-diphenylalanyl-L-prolyl-[(4-amidino-3-aminophenyl)methyl]amide,
15. N-aminosulfonyl-D-diphenylalanyl-L-prolyl-[(4-amidino-3-methoxyphenyl)methyl]amide,
16. N-t-butoxycarbonyl-D-diphenylalanyl-L-prolyl-[(4-amidinophenyl)methyl]amide,
17. N-methoxycarbonyl-D-diphenylalanyl-L-prolyl-[(4-amidinophenyl)methyl]amide,
18. N-propyloxycarbonyl-D-diphenylalanyl-L-prolyl-[(4-amidinophenyl)methyl]amide,
19. N-benzyloxycarbonyl-D-diphenylalanyl-L-prolyl-[(4-amidinophenyl)methyl]amide,
20. N-phenyloxycarbonyl-D-diphenylalanyl-L-prolyl-[(4-amidinophenyl)methyl]amide,
21. N-methoxycarbonyl-D-dicyclohexylalanyl-L-prolyl-[(4-amidinophenyl)methyl]amide,
22. N-methoxycarbonyl-D-diphenylalanyl-L-azetidine-2-carboxyl-[(4-amidinophenyl)methyl]amide,
23. N-methoxycarbonyl-D-diphenylalanyl-L-prolyl-(6-amidino-3-picolyl) amide,
24. N-methoxycarbonyl-D-dicyclohexylalanyl-L-prolyl-(6-amidino-3-picolyl) amide,
25. N-methoxycarbonyl-D-diphenylalanyl-L-prolyl-(5-amidino-2-picolyl) amide,
26. N-methoxycarbonyl-D-diphenylalanyl-L-prolyl-[(2-amidino-5-pyrimidyl)methyl]amide,
27. N-methoxycarbonyl-D-diphenylalanyl-L-prolyl-[(4-amidino-3-fluorophenyl)methyl]amide,
28. N-methoxycarbonyl-D-diphenylalanyl-L-prolyl-[(4-amidino-3-methoxyphenyl)methyl]amide,
29. N-methoxycarbonyl-D-diphenylalanyl-L-prolyl-[(4-amidino-3-methylphenyl)methyl]amide,
30. N-acetyl-D-diphenylalanyl-L-prolyl-[(4-amidinophenyl)methyl]amide,
31. D-diphenylalanyl-L-prolyl-[(4-amidinophenyl)methyl] amide,
32. N-methylsulfonyl-D-diphenylalanyl-L-prolyl-[(4-amidinophenyl)methyl]amide,
33. N-benzylsulfonyl-D-diphenylalanyl-L-prolyl-[(4-amidinophenyl)methyl]amide,
34. N-dimethylaminosulfonyl-D-diphenylalanyl-L-prolyl-[(4-amidinophenyl)methyl]amide,
35. N-dimethoxyphosphoryl-D-diphenylalanyl-L-prolyl-[(4-amidinophenyl)methyl]amide,
36. N-dimethylphosphoryl-D-diphenylalanyl-L-prolyl-[(4-amidinophenyl)methyl]amide,
37. N-carboxymethyl-D-diphenylalanyl-L-prolyl-[(4-amidinophenyl)methyl]amide,
38. N-carboxymethyl-D-diphenylalanyl-L-prolyl-(6-amidino-3-picolyl)amide,
39. N-carboxymethyl-D-diphenylalanyl-L-prolyl-[(4-amidino-3-fluorophenyl)methyl]amide,
40. N-carboxymethyl-D-diphenylalanyl-L-prolyl-[(4-amidino-3-methylphenyl)methyl]amide,
41. N-(ethoxycarbonyl)methyl-D-diphenylalanyl-L-prolyl-[(4-hydroxyamidinophenyl)methyl]amide,
42. N-phenyl-D-diphenylalanyl-L-prolyl-[(4-amidinophenyl)methyl]amide.

The compound of agents of the present invention may be prepared using the reaction routes and synthesis schemes as described below, employing the techniques available in the art using starting materials that are readily available.

The amidine compounds (formula Ia) can be prepared from the compounds of formula II by a three-step sequence involving sequential treatment with hydrogen sulfide, methyl iodide, and ammonium acetate or by two-step sequence involving treatment with hydroxylamine hydrochloride in the presence of base such as sodium carbonate and catalytic hydrogenation of the resultant amidoxime in the presence of acetic anhydride. Alternatively, the compounds of formula Ia can be prepared by deprotection of the compounds of formula III. The methylamine compounds (formula Ib) can be prepared by catalytic hydrogenation of the compounds of formula II in the presence of a strong acid such as hydrochloric acid.

Formula Ia:

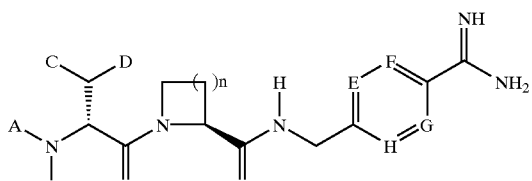

Formula Ib:

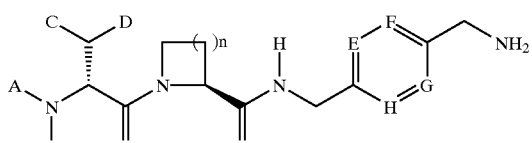

Formula II:

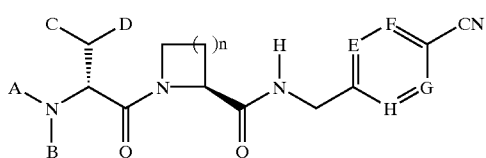

Formula III:

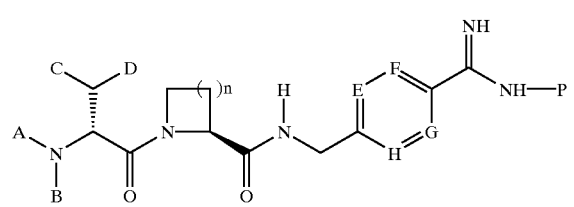

In the above structural formula, A—H, and n are same as previously defined, and P is a protecting group such as t-butoxycarbonyl (Boc), benzyloxycarbonyl (Cbz), and p-toluenesulfonyl.

Compounds of formula II can be prepared according to the general procedure outlined in Scheme 1 through 3.

As exemplified by Example 1 (Scheme 1), a protected amino acid such as N-Boc-D-diphenylalnine is coupled to proline methyl ester using a coupling agent such as EDC and HOBT. The resultant dipeptide is treated with a strong acid such as hydrochloric acid gas or trifluoroacetic acid to remove the t-butoxycarbonyl (Boc) protecting group. The resultant free amine is reacted with a sulfonylating reagent such as sulfamoyl chloride and a base such as triethylamine. Carbamate-containing compounds are prepared using chloroformates. The product is then hydrolyzed with base such as lithium hydroxide, and the resultant acid is coupled to the desired amine such as 4-aminomethylbenzonitrile.

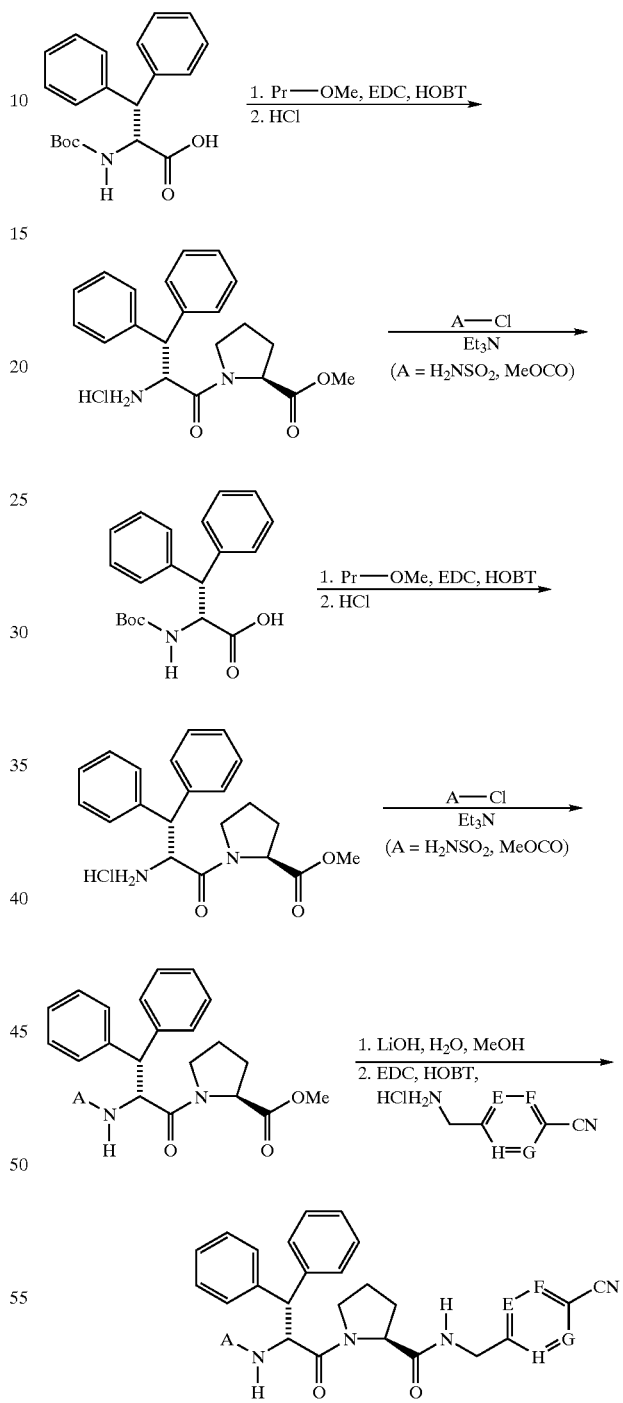

An alternative route, as depicted in Scheme 2, is to hydrolyze the Boc-protected dipeptide before functionalizing the amino group and then couple the resultant acid with the desired amine. The protecting group of the coupling product is removed and the free amine is then sulfonylated.

Scheme 2

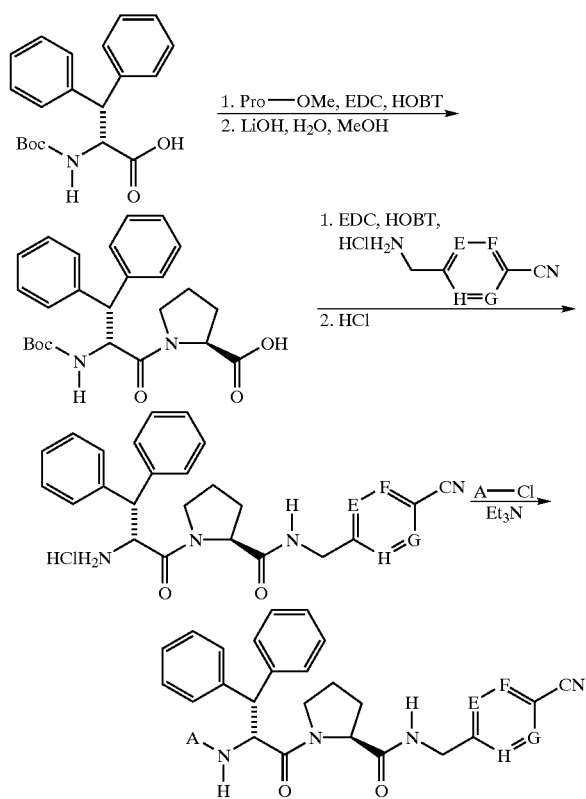

N-Boc-D-diphenylalnine can be coupled directly to the amine-coupled proline as exemplified by Example 5 (Scheme 3). The product is then deprotected and subsequently sulfonylated.

Scheme 3

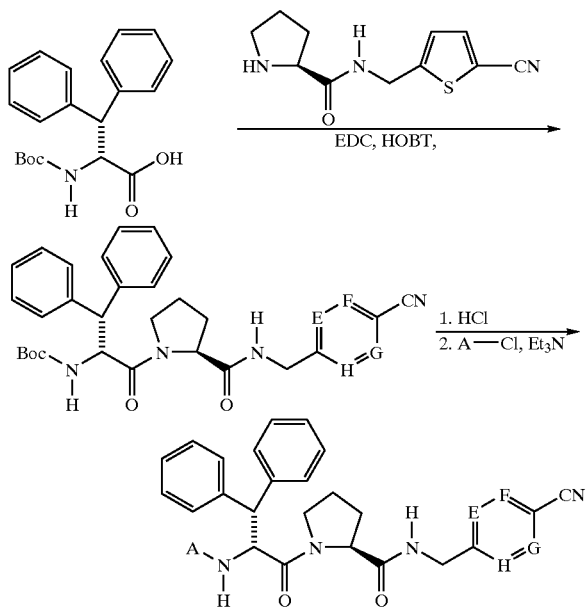

Compounds of formula III can be prepared according to the general procedure outlined in Scheme 4.

Scheme 4

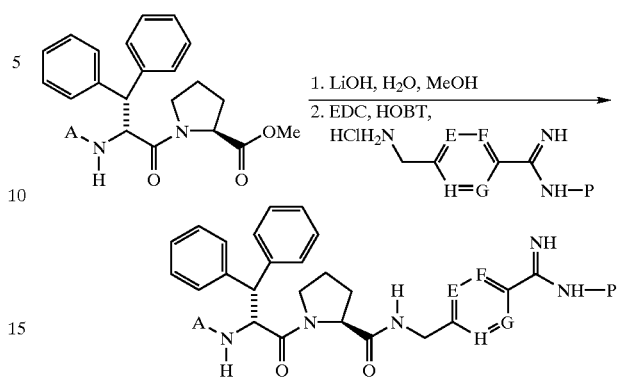

Amide coupling used to form the compounds of this invention are typically performed by the carbodiimide method with reagents such as dicyclohexylcarbodiimide (DCC) or 1-ethyl-3-(3-dimethylaminopropyl) carbodiimide (EDC). Other method for forming the amide or peptide bond include, but not limited to the synthetic routes via an acid chloride, azide, mixed anhydride or activated ester. The addition and removal of one or more protecting groups are typical practice. Methods for suitable protection and deprotection are provided in "Protective Groups in Organic Synthesis", 3rd Edition, by T. W. Green and Peter G. M. Wuts (1999), John Wiley & Sons, Inc., publishers.

The amide coupling reactions are carried out in an inert organic solvent such as dimethylformamide, dimethylacetamide, tetrahydrofuran, dichloromethane, chloroform, and like common solvents or a mixture of such solvents.

Compounds that potently regulate, modulate, or inhibit the conversion of fibrinogen to fibrin via the enzyme thrombin, and therefore inhibit thrombosis and clotting are desirable and represent preferred embodiments of the present invention. The present invention is further directed to methods of modulating trypsin-like serine protease activity, for example in mammalian tissue, by administering an inventive agent. The activity of the compounds of the present invention as modulators of trypsin-like serine protease activity, such as the activity of thrombin, may be measured by any of the methods available to those skilled in the art, including in vivo and/or in vitro assays. These properties may be assessed, for example, by using one or more of the biological testing procedures set out in the examples below.

The active agents of the present invention may be formulated into pharmaceutical compositions as described below. Pharmaceutical compositions of the present invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving modulation of tyrpsin-like serine proteases. By "efficacious levels" is meant levels in which the effects of tyrpsin-like serine proteases like thrombin are, at a minimum, regulated. These compositions are prepared in unit-dosage form appropriate for the mode of administration, e.g., parenteral or oral administration.

The pharmaceutical compositions of the present invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

The pharmaceutical compositions of the present invention also may comprise suitable solid- or gel-phase carriers or excipients. Examples of such carriers or excipients include calcium carbonate, calcium phosphate, sugars, starches, cellulose derivatives, gelatin, and polymers such as polyethylene glycols. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, and most preferably 1–20 mg/kg, with courses of treatment repeated at appropriate intervals. Administration of prodrugs are typically dosed at weight levels which are chemically equivalent to the weight levels of the fully active form. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form vial topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

Therapeutically effective amounts of the agents of the invention may be used to treat diseases mediated by modulation or regulation of trypsin-like serine proteases. An "effective amount" is intended to mean that amount of an agent that, when administered to a mammal in need of such treatment, is sufficient to effect treatment for a disease mediated by the activity of one or more trypsin-like serine proteases, such as thrombin. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more trypsin-like serine proteases, such as thrombin, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Proper formulation is dependent upon the route of administration chosen. The inventive compounds may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

For injection, the agents of the present invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems.

Some abbreviations that appear in this application are as follows.

| | |
|---|---|
| Boc: | t-butoxycarbonyl |
| Pro: | proline |
| EDC: | 1-ethyl-3-(3-dimethylaminopropyl)carbodiimide hydrochloride |
| HOBT: | 1-hydroxybenzonitrile hydrate |
| TFA: | trifluoroacetic acid |
| AcOH: | acetic acid |
| DMF: | dimethylformamide |
| EtOAc: | ethyl acetate |
| HCl: | hydrochloride |
| rt: | room temperature |
| TEA: | triethylamine |
| FAB MS: | fast atom bombardment mass spectrum |

The present invention will be more specifically illustrated by the following examples but it should be understood that the present invention is not limited to those examples in any manner. The compound number used in the following examples denotes the compound number described in the following Table I.

The preparation processes of preferred compounds of the present invention are described in detail in the following examples, but the artisan will recognize that the chemical reactions described may be readily adapted to prepare a number of other thrombin inhibitors of the invention. For example, the synthesis of non-exemplified compounds according to the invention may be successfully performed by modifications apparent to those skilled in the art, e.g. by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLE 1

Preparation of N-aminosulfonyl-D-diphenylalanyl-L-prolyl-[(4-amidinophenyl)methyl]amide.TFA

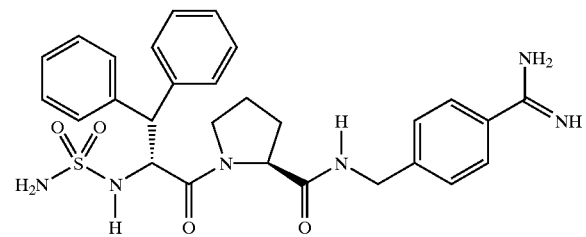

A) N-Aminosulfonyl-D-diphenylalanyl-L-proline methyl ester

To a stirring solution of chlorosulfonyl isocyanate (6.3 g, 45 mmol) in dichloromethane (25 mL) was added dropwise formic acid (2.13 g, 45 mmol). The mixture was heated at reflux for 5 h and cooled to obtain 1.8 N solution of sulfamoyl chloride in dichloromethane. To a cooled (0° C.) solution of D-diphenylalanyl-L-proline methyl ester.HCl (2.5 g, 6.47 mmol) in dichloromethane (100 mL) was added the 1.8 N sulfamoylchloride solution (6 mL) and triethylamine (2.7 mL). After the reaction was completed, the resulting solution was diluted with dichloromethane (40 mL), washed with brine, dried over magnesium sulfate, and concentrated in vacuo. The residue was purified by column chromatography (EtOAc:n-hexane, 2:1) to give the title compound (1.88 g, 67%).

$^1$H NMR (CDCl$_3$) δ 7.38–7.20 (m, 4H), 7.18 (m, 6H), 5.85 (d, 1H), 5.29 (s, 2H), 4.95 (dd, 1H), 4.75 (m, 1H), 4.14 (d, 1H), 3.67 (s, 3H), 2.70 (m, 1H), 1.74 (m, 3H), 1.38 (m, 1H).

FAB MS: 431 [M+1]$^+$

B) N-Aminosulfonyl-D-diphenylalanyl-L-proline

To a suspension of N-aminosulfonyl-D-diphenylalanyl-L-proline methyl ester (1.88 g, 4.36 mmol) in a mixture of water (100 mL) and methanol (150 mL) was added 0.5 N lithium hydroxide (40 mL) and the mixture stirred overnight at rt. The resulting solution was acidified to pH 2 by addition of 1N HCl and the solvent partially removed by evaporation in vacuo. The precipitates were collected by filtration to give the title compound as a white crystalline solid (1.68 g, 92%).

$^1$H NMR (CD$_3$OD) δ 7.40 (m, 2H), 7.33 (m, 2H), 7.24 (m, 6H), 4.95 (dd, 1H), 4.29 (d, 1H), 4.05 (m, 1H), 3.75 (m, 1H), 2.87 (m, 1H), 1.83–1.72 (m, 3H), 1.43 (m, 1H).

FAB MS: 418 [M+1]$^+$

C) N-Aminosulfonyl-D-diphenylalanyl-L-prolyl-[(4-cyanophenyl)methyl]amide

A mixture of N-aminosulfonyl-D-diphenylalanyl-L-proline (0.7 g, 1.4 mmol), 4-aminomethylbenzonitrile.HCl (0.26 g, 1.56 mmol), EDC (0.54 g, 2.8 mmol), HOBT (0.3 g, 2.1 mmol), and N-methylmorpholine (0.6 mL, 4.26 mmol) in DMF (10 mL) was stirred for 2 h at rt. The solvent was removed in vacuo and the residue dissolved in EtOAc and washed sequentially with a saturated sodium bicarbonate solution, 1N HCl, and brine. After the solution was dried over magnesium sulfate and concentrated in vacuo, the residue was purified by column chromatography (EtOAc:n-hexane, 1:1) to give the title compound (0.65 g, 87%).

$^1$H NMR (CDCl$_3$) δ 1.42 (m, 1H), 1.52 (m, 1H), 1.75 (m, 1H), 1.98 (m, 1H), 2.63 (m, 1H), 3.63 (m, 1H), 4.17 (m, 1H), 4.28–4.49 (m, 3H), 4.86–4.90 (m, 3H), 5.51 (m, 1H), 7.20–7.45 (m, 12H), 7.58 (m, 2H).

FAB MS: 532[M+1]$^+$

D) N-Aminosulfonyl-D-diphenylalanyl-L-prolyl-[(4-amidinophenyl)methyl]amide.TFA

A solution of the coupling compound obtained in Step C (0.64 g, 1.37 mmol) in a mixture of pyridine (10 mL) and triethylamine (2 mL) was saturated with gaseous H$_2$S. After the mixture was allowed to stand for 1 day, the solvent was removed in vacuo to obtain the thioamide as a yellow solid. To this material was added acetone (10 mL) and iodomethane (0.26 mL, 4.18 mmol), and the mixture was heated at reflux for 2 h. After the solvent was evaporated in vacuo, the resulting methylthioamidate was dissolved in acetonitrile (2 mL). To this solution was added ammonium acetate (0.32 g, 4.15 mmol) and the mixture heated at reflux for 1 h. The solution was cooled and concentrated and the residue purified by column chromatography using 10% methanol in chloroform to give the title compound which was further purified by preparative HPLC (H$_2$O-MeOH gradient). The pure fractions were lyophilized to give a white solid (0.27 g, 41%) as a TFA salt.

$^1$H NMR (CD$_3$OD) δ 1.46 (m, 1H), 1.61 (m, 1H), 1.71 (m, 1H), 1.85 (m, 1H), 2.91 (m, 1H), 3.78 (m, 1H), 4.09 (m, 1H), 4.31–4.39 (m, 2H), 4.45 (m, 1H), 4.91 (m, 1H), 7.18–7.55 (m, 12H), 7.73 (m, 2H).

FAB MS: 549 [M+1]$^+$

EXAMPLE 2

Preparation of N-aminosulfonyl-D-diphenylalanyl-L-prolyl-[(4-aminomethylphenyl)methyl]amide.HCl

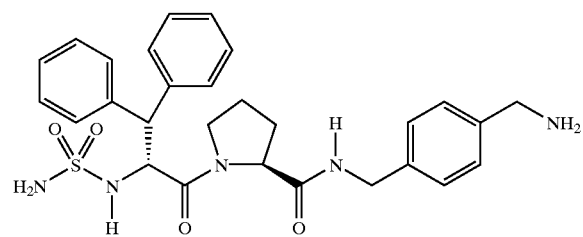

N-Aminosulfonyl-D-diphenylalanyl-L-prolyl-[(4-cyanophenyl)methyl]amide prepared in Example 1, Step C (200 mg, 0.43 mmol) was dissolved in methanol (2 mL). To this solution was added 10% palladium-on-carbon (100 mg) and 3 drops of conc. HCl and the mixture stirred for 6 h under H$_2$ (Parr reactor, 50 psi). The reaction mixture was filtered through Celite and the filtrate concentrated in vacuo. The residue was purified by preparative HPLC (TFA (0.1%)-H$_2$O—MeOH gradient) to give the title compound (170 mg, 86%) as a white solid.

$^1$H NMR (CD$_3$OD) δ 1.36 (m, 1H), 1.61 (m, 1H), 2.76 (m, 2H), 2.92 (m, 1H), 3.70 (m, 1H), 4.07 (m, 3H), 4.35 (m, 3H), 5.02 (m, 1H), 7.20–7.54 (m, 14H).

FAB MS: 536 [M+1]$^+$

EXAMPLE 3

Preparation of N-aminosulfonyl-D-3,4-dichlorophenylalanyl-L-prolyl-[(4-amidinophenyl) methyl]amide.TFA

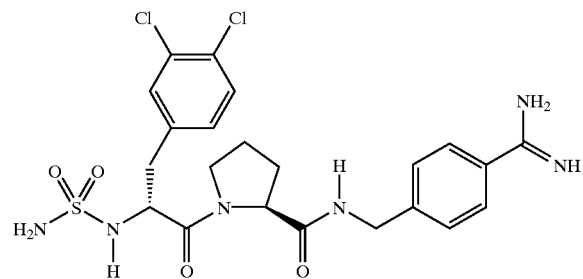

A) N-Aminosulfonyl-D-3,4-dichlorophenylalanyl-L-proline

The title compound was prepared from D-3,4-dichlorophenylalanyl-L-proline methyl ester using the procedure described in Example 1, Step A and B; yield 60%.

$^1$H NMR (CD$_3$OD) δ 1.30 (m, 1H), 1.74 (m, 1H), 1.88–1.93 (m, 2H), 2.78 (m, 3H), 3.71 (m, 1H), 4.30–4.42 (m, 2H), 5.23 (m, 1H), 7.11–7.42 (m, 3H).

FAB MS: 411 [M+1]$^+$

B) N-Aminosulfonyl-D-3,4-dichlorophenylalanyl-L-prolyl-[(4-amidinophenyl)methyl]amide.TFA The title compound was prepared from the compound obtained Step A using the procedure described in Example 1, Step C and D; yield 30%.

$^1$H NMR (CD$_3$OD) δ 1.28 (m, 1H), 1.75 (m, 1H), 1.90 (m, 1H), 2.00 (m, 1H), 2.98 (m, 2H), 3.07 (m, 1H), 3.82 (m, 1H), 4.36–4.61 (m, 4H), 7.23 (m, 1H), 7.44–7.53 (m, 4H), 7.78 (m, 2H).

FAB MS: 542 [M+1]$^+$

EXAMPLE 4

Preparation of N-aminosulfonyl-D-dicyclohexylalanyl-L-prolyl-[(4-amidinophenyl) methyl]amide.TFA

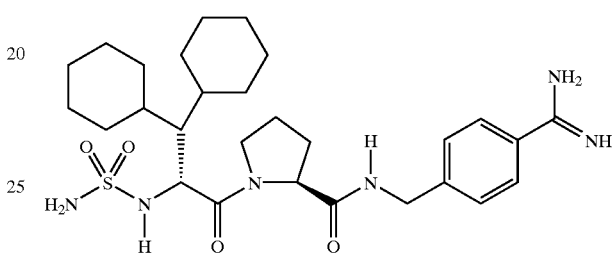

The title compound was prepared from D-dicyclohexylalanyl-L-proline methyl ester.HCl (see *J. Med. Chem.* 1997, 40, 3726) using the procedure described in Example 1; yield 16%.

$^1$H NMR (CD$_3$OD) δ 1.07–2.18 (m, 27H), 3.31 (m, 1H), 3.79 (m, 1H), 4.18–4.53 (m, 3H), 5.07 (m, 1H), 7.50 (m, 2H), 7.71 (m, 2H).

FAB MS: 561 [M+1]$^+$

EXAMPLE 5

Preparation of N-aminosulfonyl-D-diphenylalanyl-L-azetidine-2-carboxyl-[(4-amidinophenyl)methyl] amide.TFA

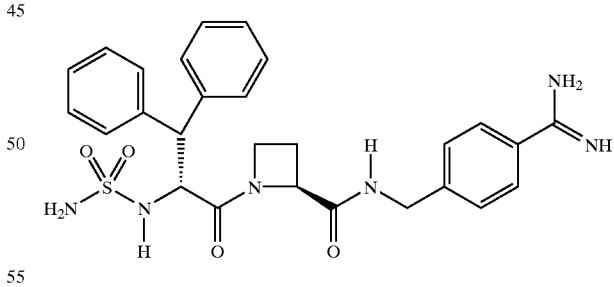

A) N-Boc-L-azetidine-2-carboxyl-[(4-cyanophenyl) methyl]amide

To a cooled (0° C.) solution of N-Boc-L-2-azetidinecarboxylic acid (0.5 g, 2.49 mmol) in DMF (3 mL) was added 4-aminomethylbenzonitrile.HCl (0.46 g, 2.74 mmol), EDC (0.62 g, 3.24 mmol), HOBT (0.40 g, 2.99 mmol), and triethylamine (1.04 mL, 7.47 mmol) and the mixture stirred for 2 h at rt. The solvent was removed in vacuo and the residue dissolved in EtOAc, washed sequentially with a saturated sodium bicarbonate solution, 1N HCl, and brine. After the solution was dried over magnesium sulfate and concentrated in vacuo, the residue was purified by column chromatography (EtOAc:n-hexane, 2:1) to give the title compound (0.66 g, 84%).

FAB MS: 316 [M+1]⁺

B) N-Boc-D-diphenylalanyl-L-azetidine-2-carboxyl-[(4-cyanophenyl)methyl]amide

To a cooled (0° C.) solution of the compound prepared in Step A (1.4 g, 2.37 mmol) in dichloromethane (15 mL) was added TFA (15 mL) and the mixture stirred for 3 h at rt. The resulting solution was concentrated in vacuo to give Boc-deprotected compound as TFA salt (0.72 g, 93%). This product (0.2 g, 0.6 mmol) was dissolved in DMF (6 mL), and to this solution was added Boc-D-diphenylalanine (0.18 g, 0.54 mmol), EDC (0.13 g, 0.7 mmol), HOBT (0.09 g, 0.54 mmol). The mixture was stirred until clear and then cooled to 0° C. After triethylamine was added (0.3 mL, 2.16 mmol), the resulting mixture was stirred for additional 2 h at rt. The solvent was removed in vacuo and the residue dissolved in EtOAc, washed sequentially with a saturated sodium bicarbonate solution, 1N HCl, and brine. After the solution was dried over magnesium sulfate and concentrated in vacuo, the residue was purified by column chromatography (EtOAc:n-hexane, 2:1) to give the title compound (0.25 g, 88%).

FAB MS: 539 [M+1]⁺

C) N-Aminosulfonyl-D-diphenylalanyl-L-azetidine-2-carboxyl-[(4-amidinophenyl)methyl]amide.TFA This compound was prepared from the compound obtained in Step B using the same procedure as described in Example 1, Step A and D; yield 47%.

¹H NMR (CD₃OD) δ 2.54 (m, 1H), 2.83 (m, 2H), 2.89 (m, 1H), 3.75 (m, 1H), 4.02 (m, 1H), 4.30–4.37 (m, 2H), 4.41 (m, 1H), 4.87 (m, 1H), 7.16–7.52 (m, 12H), 7.70 (m, 2H).

FAB MS: 535 [M+1]⁺

EXAMPLE 6

Preparation of N-aminosulfonyl-D-cyclohexylglycinyl-L-prolyl-[(4-amidinophenyl)methyl]amide.TFA

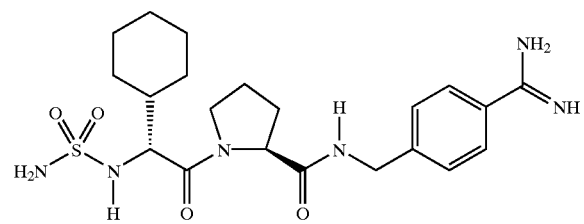

This compound was prepared from D-cyclohexylglycinyl-L-proline methyl ester essentially according to the procedure of Example 1; yield 17%.

¹H NMR (CD₃OD) δ 0.93–1.88 (m, 14H), 2.15 (m, 1H), 3.12 (m, 1H), 3.95 (m, 1H), 4.37–4.62 (m, 3H), 4.92 (m, 1H), 7.40 (m, 2H), 7.72 (m, 2H).

FAB MS: 465[M+1]⁺

EXAMPLE 7

Preparation of N-aminosulfonyl-D-cyclohexylalanyl-L-prolyl-[(4-amidinophenyl)methyl]amide.TFA

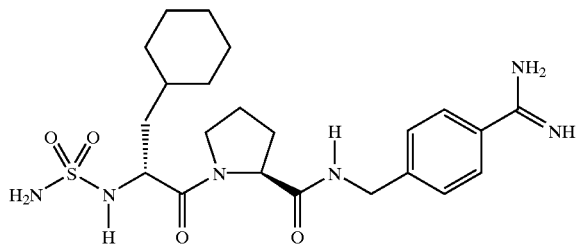

This compound was prepared from D-cyclohexylalanyl-L-proline methyl ester essentially according to the procedure of Example 1; yield 22%.

¹H NMR (CD₃OD) δ 0.78–1.0 (m, 2H), 1.10–1.81 (m, 10H), 1.85–2.23 (m, 5H), 3.49 (m, 1H), 3.83 (m, 1H), 4.30–4.55 (m, 3H), 5.05 (m, 1H), 7.42 (m, 2H), 7.68 (m, 2H).

FAB MS: 479 [M+1]⁺

EXAMPLE 8

Preparation of N-Aminosulfonyl-D-valinyl-L-prolyl-[(4-amidinophenyl)methyl]amide.TFA

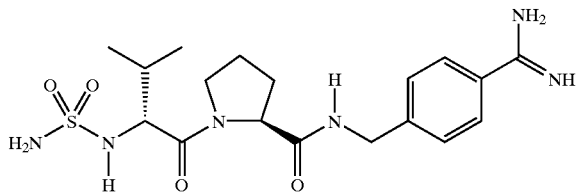

This compound was prepared from D-valinyl-L-proline methyl ester essentially according to the procedure of Example 1; yield 17%.

¹H NMR (CD₃OD) δ 1.15 (m, 6H), 1.40 (m, 1H), 1.68–1.72 (m, 2H), 1.87 (m, 1H), 2.38 (m, 1H), 3.25 (m, 1H), 3.81 (m, 1H), 4.25–4.63 (m, 3H), 5.20 (m, 1H), 7.47 (m, 2H), 7.70 (m, 2H).

FAB MS: 425 [M+1]⁺

EXAMPLE 9

Preparation of N-aminosulfonyl-D-diphenylalanyl-L-prolyl-(6-amidino-3-picolyl)amide.TFA

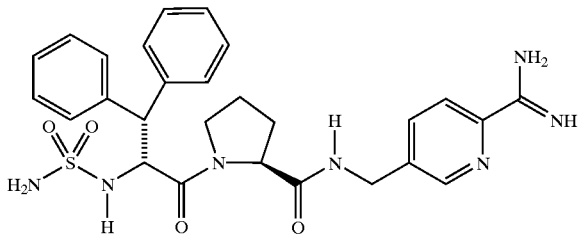

A) 6-Cyano-3-picoline

A mixture of 6-bromo-3-picoline (3 g, 17.4 mmol) and cuprous cyanide (2.3 g, 26.1 mmol) in DMF (60 mL) was heated at reflux for 1.5 h. The reaction mixture was diluted with dichloromethane, washed with aqueous ammonia, dried over magnesium sulfate, and concentrated in vacuo. The residue was purified by column chromatography (EtOAc:n-hexane, 1:9) to give the title compound (1.6 g, 78%).

$^1$H NMR (CDCl$_3$) δ 8.51 (s, 1H), 7.66 (d, 1H), 7.40 (d, 1H), 2.41 (s, 3H).

FAB MS: 119 [M+1]$^+$

B) 6-Cyano-3-picolylbromide

A mixture of 6-cyano-3-picoline (1.32 g, 11.19 mmol), benzoylperoxide (0.54 g, 2.24 mmol), and N-bromosuccinimide (2.8 g, 15.7 mmol) in carbontetrachloride (30 mL) was heated at reflux for 2 h. The resulting suspension was filtered and the filtrate diluted with dichloromethane (400 mL), washed with a saturated sodium bicarbonate solution, dried over magnesium sulfate, and concentrated in vacuo. The residue was purified by column chromatography (EtOAc:n-hexane, 1:9) to give the title compound as a yellow oil (1.12 g, 51%).

$^1$H NMR (CDCl$_3$) δ 8.64 (s, 1H), 7.76 (d, 1H), 7.63 (d, 1H), 4.55 (s, 2H).

FAB MS: 197 [M+1]$^+$

C) 6-Cyano-3-picolylamine.HCl

To a cold solution of 6-cyano-3-picolylbromide (1.06 g, 5.4 mmol) in THF (10 mL) was added sodium hydride (60% dispersion in oil, 0.24 g, 6 mmol) in portions. To this suspension was added di-t-butyl iminodicarboxylate (0.65 g, 3 mmol) in portions. After stirring for 3 h, the resulting solution was diluted with ethyl acetate, washed with water, dried over magnesium sulfate, and concentrated in vacuo. The residue was purified by column chromatography (EtOAc:n-hexane, 1:9) to give 5-(N,N-Boc$_2$-aminomethyl)pyridine-2-carbonitrile (580 mg). This solid was dissolved in methanol (20 mL) and cooled to 0° C. HCl gas was bubbled through the solution for 10 min, and the mixture was allowed to warmed to room temperature. The solvent was removed in vacuo to give the title compound as a white solid (293 mg, 53%).

$^1$H NMR (CD$_3$OD) δ 8.54 (s, 1H), 7.56 (d, 1H), 7.43 (d, 1H), 4.80 (s, 2H).

FAB MS: 133 [M+1]$^+$

D) N-Aminosulfonyl-D-diphenylalanyl-L-prolyl-(6-amidino-3-picolyl)amide.TFA

This compound was prepared from 6-cyano-3-picolylamine.HCl and N-aminosulfonyl-D-diphenylalanyl-L-proline using the procedure described in Example 1, Step C and D; yield 44%.

$^1$H NMR (CD$_3$OD) δ 8.72 (s, 1H), 8.08 (d, 1H), 7.99 (d, 1H), 7.44–7.35 (m, 4H), 7.26–7.24 (m, 6H), 4.98 (d, 1H), 4.55 (dd, 1H), 4.33–4.30 (m, 2H), 4.06 (dd, 1H), 3.76 (m, 1H), 2.9 (m, 1H), 1.84–1.4 (m, 4H).

FAB MS: 550 [M+1]$^+$

EXAMPLE 10

Preparation of N-aminosulfonyl-D-diphenylalanyl-L-prolyl-(6-aminomethyl-3-picolyl)amide

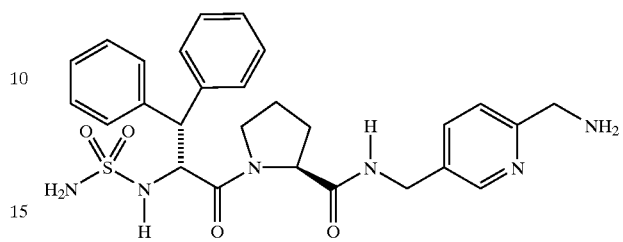

This compound was prepared from N-aminosulfonyl-D-diphenylalanyl-L-prolyl-(6-cyano-3-picolyl)amide (see Example 9) essentially using the procedure described in Example 2; yield 75%.

$^1$H NMR (CD$_3$OD) δ 8.26 (s, 1H), 8.07 (d, 1H), 8.00 (d, 1H), 7.52 (m, 4H), 7.36–7.19 (m, 6H), 5.02 (d, 1H), 4.64 (m, 3H), 4.31 (m, 1H), 4.09 (s, 2H), 3.75 (m, 1H), 2.80 (m, 1H), 1.90–1.45 (m, 4H).

FAB MS: 537 [M+1]$^+$

EXAMPLE 11

Preparation of N-aminosulfonyl-D-dicyclohexylalanyl-L-prolyl-(6-amidino-3-picolyl)amide.TFA

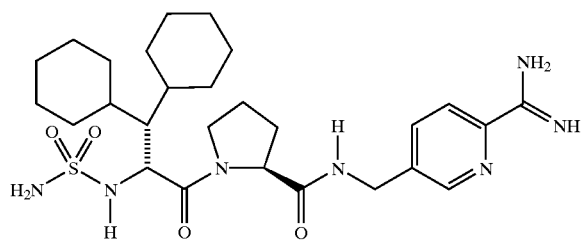

This compound was prepared from D-dicyclohexylalanyl-L-proline methyl ester and 6-cyano-3-picolylamine.HCl essentially according to the procedure of Example 1.

$^1$H NMR (CD$_3$OD) δ 8.72 (s, 1H), 8.08 (d, 1H), 7.99 (d, 1H), 5.07 (m, 1H), 4.18–4.53 (m, 3H), 3.79 (m, 1H), 3.31 (m, 1H), 2.18–1.07 (m, 27H).

FAB MS: 562 [M+1]$^+$

EXAMPLE 12

Preparation of N-aminosulfonyl-D-cyclohexylalanyl-L-prolyl-(6-amidino-3-picolyl)amide.TFA

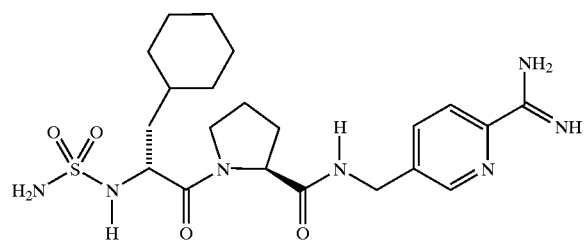

This compound was prepared from D-cyclohexylalanyl-L-proline methyl ester and 6-cyano-3-picolylamine.HCl essentially according to the procedure of Example 1.

$^1$H NMR (CD$_3$OD) δ 8.67(s, 1H), 8.04 (d, 1H), 7.89(d, 1H), 5.05(m, 1H), 4.55–4.30 (m, 3H), 3.83(m, 1H), 3.49(m, 1H), 2.23–1.85(m, 5H), 1.81–1.10(m, 10H), 1.01–0.78(m, 2H).

FAB MS: 480 [M+1]$^+$

EXAMPLE 13

Preparation of N-aminosulfonyl-D-diphenylalanyl-L-prolyl-(5-amidino-2-picolyl)amide.TFA

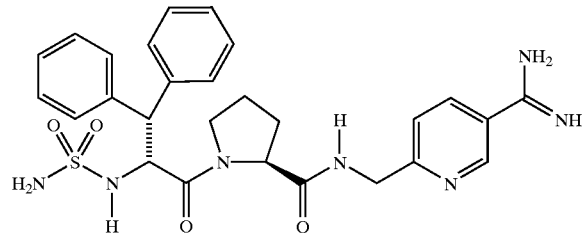

A) 5-Cyano-2-picolylamine.HCl

This compound was prepared from 5-cyano-2-picoline.HCl using the procedure described in Example 9, Step B and C; yield 41%.

$^1$H NMR (CD$_3$OD) δ 8.70 (s, 1H), 7.76 (d, 1H), 7.53 (d, 1H), 4.80 (s, 2H).

FAB MS: 133 [M+1]$^+$

B) N-Aminosulfonyl-D-diphenylalanyl-L-prolyl-(5-amidino-2-picolyl)amide.TFA

This compound was prepared from 5-cyano-2-picolylamine.HCl and N-aminosulfonyl-D-diphenylalanyl-L-proline using the procedure described in Example 1, Step C and D; yield 52%.

$^1$H NMR (CD$_3$OD) δ 8.82 (s, 1H), 8.18 (d, 1H), 8.03 (d, 1H), 7.44–7.35 (m, 4H), 7.26–7.24 (m, 6H), 5.01 (d, 1H), 4.55 (dd, 1H), 4.33–4.30 (m, 2H), 4.06 (dd, 1H), 3.76 (m, 1H), 2.90 (m, 1H), 1.84–1.45 (m, 4H).

FAB MS: 550 [M+1]$^+$

EXAMPLE 14

Preparation of N-aminosulfonyl-D-diphenylalanyl-L-prolyl-[(2-amidino-5-pyrimidyl)methyl]amide.TFA

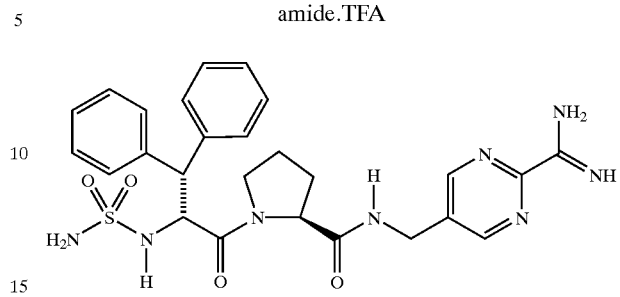

This compound was prepared from D-diphenylalanyl-L-proline methyl ester and 5-aminomethylpyrimidine-2-carbonitrile.HCl (WO9625426) essentially according to the procedure of Example 1.

$^1$H NMR (CD$_3$OD) δ 8.72 (m, 2H), 7.44–7.35 (m, 4H), 7.26–7.24 (m, 6H), 5.02 (d, 1H), 4.55 (dd, 1H), 4.33–4.30 (m, 2H), 4.06 (dd, 1H), 3.76 (m, 1H), 2.90 (m, 1H), 1.84–1.45 (m, 4H).

FAB MS: 551 [M+1]$^+$

EXAMPLE 15

Preparation of N-aminosulfonyl-D-diphenylalanyl-L-prolyl-[(4-amidino-3-fluorophenyl)methyl]amide.TFA

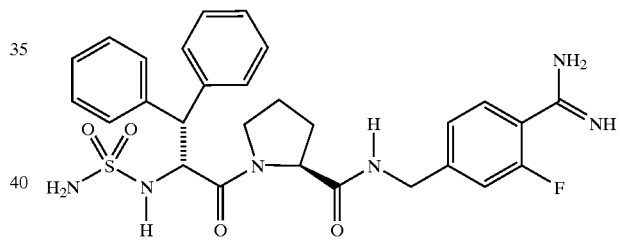

A) 2-Fluoro-4-methylbenzonitrile

A mixture of 4-bromo-3-fluorotoluene (2 g, 10.6 mmol) and cuprous cyanide (1.4 g, 15.9 mmol) in DMF (15 mL) was heated at reflux for 4 h. The reaction mixture was diluted with ethyl acetate, washed with aqueous ammonia, dried over magnesium sulfate, and concentrated in vacuo. The residue was purified by column chromatography (EtOAc:n-hexane, 1:4) to give the title compound (1.0 g, 70%).

$^1$H NMR (CDCl$_3$) δ 7.50 (m, 1H), 7.08 (m, 2H), 2.45 (s, 3H).

FAB MS: 136 [M+1]$^+$

B) 4-Bromomethy-2-fluorobenzonitrile

A mixture of 2-fluoro-4-methylbenzonitrile (1 g, 7.4 mmol), benzoylperoxide (0.39 g, 1.6 mmol), and N-bromosuccinimide (1.9 g, 10.6 mmol) in carbontetrachloride (100 mL) was heated at reflux for 3 h. The resulting suspension was filtered and the filtrate diluted with dichloromethane, washed with a saturated sodium bicarbonate solution, dried over magnesium sulfate, and concentrated in vacuo. The residue was purified by column chromatography (EtOAc:n-hexane, 1:9) to give the title compound as a yellow oil (0.9 g, 56%).

¹H NMR (CDCl₃) δ 7.41 (m, 1H), 7.30 (m, 2H), 4.55 (s, 2H).

FAB MS: 215 [M+1]⁺

C) 4-Cyano-3-fluorobenzylamine.HCl

This compound was prepared from 4-bromomethy-2-fluorobenzonitrile essentially according to the procedure of Example 9, Step C; yield 78%.

¹H NMR (CD₃OD) δ 7.49 (m, 1H), 7.20 (m, 2H), 4.12 (s, 2H).

FAB MS: 151 [M+1]⁺

D) N-Aminosulfonyl-D-diphenylalanyl-L-prolyl-[(4-amidino-3-fluorophenyl)methyl]amide.TFA This compound was prepared from 4-cyano-3-fluorobenzylamine.HCl and N-aminosulfonyl-D-diphenylalanyl-L-proline using the procedure described in Example 1, Step C and D; yield 44%.

¹H NMR (CD₃OD) δ 1.47 (m, 1H), 1.61 (m, 1H), 1.72 (m, 1H), 1.85 (m, 1H), 2.88 (m, 1H), 3.78 (m, 1H), 4.07 (m, 1H), 4.35 (m, 2H), 4.50 (m, 1H), 5.05 (m, 1H), 7.21–7.45 (m, 12H), 7.60 (m, 1H).

FAB MS: 567 [M+1]⁺

EXAMPLE 16

Preparation of N-aminosulfonyl-D-diphenylalanyl-L-prolyl-[(4-amidino-2-fluorophenyl)methyl]amide.TFA

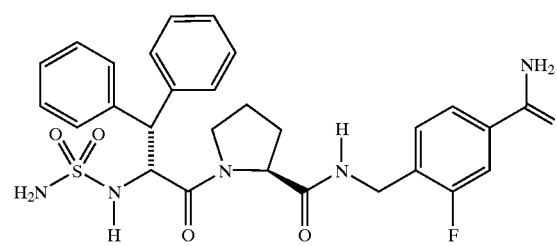

This compound was prepared using the same procedure as described in Example 15 except that 4-bromo-2-fluorotoluene was used instead of 4-bromo-3-fluorotoluene.

¹H NMR (CD₃OD) δ 1.47 (m, 1H), 1.61 (m, 1H), 1.75 (m, 1H), 1.84 (m, 1H), 2.90 (m, 1H), 3.78 (m, 1H), 4.08 (m, 1H), 4.35 (m, 2H), 4.56 (m, 1H), 4.98 (m, 1H), 7.21–7.71 (m, 13H).

FAB MS: 567 [M+1]⁺

EXAMPLE 17

Preparation of N-aminosulfonyl-D-diphenylalanyl-L-prolyl-[(4-amidino-3-methylphenyl)methyl]amide.TFA

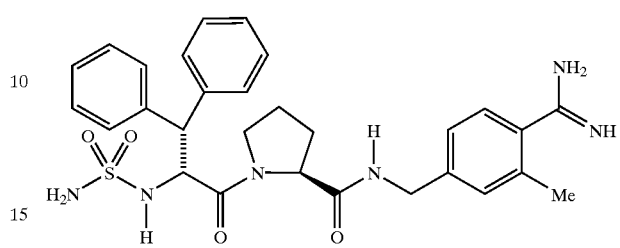

(A) 4-Bromo-3-methylbenzylamine.HCl

To a solution of borane (1.0 M BH₃ in THF, 42 mL) was added a solution of 4-bromo-3-methylbenzamide (1.3 g, 6.0 mmol) in anhydrous THF (20 mL) and the mixture stirred for 6 h at rt. To this was sequentially added dropwise 6N HCl (30 mL), water (30 mL), and MeOH (150 mL) and the mixture stirred for 12 h. After the resulting mixture was concentrated to 50 mL, the precipitates were filtered off and the filtrate concentrated in vacuo. The residue was purified by column chromatography (EtOAc: n-hexane, 1:4) to give the title compound as a yellow oil (0.81 g, 57%).

¹H NMR (CD₃OD) δ 7.60 (d, 1H), 7.37 (s, 2H), 7.18 (d, 1H), 4.04 (s, 2H), 2.41 (s, 3H).

FAB MS: 201 [M+1]⁺

B) 4-Cyano-3-methylbenzylamine.HCl

This compound was prepared from 4-bromo-3-methylbenzylamine.HCl essentially according to the procedure of Example 15, Step A; yield 44%.

¹H NMR (CD₃OD) δ 8.12 (d, 1H), 7.45 (s, 2H), 7.36 (d, 1H), 4.08 (s, 2H), 2.40 (s, 3H).

FAB MS: 147 [M+1]⁺

C) N-Aminosulfonyl-D-diphenylalanyl-L-prolyl-[(4-amidino-3-methylphenyl)methyl]amide.TFA This compound was prepared from 4-cyano-3-methylbenzylamine.HCl and N-aminosulfonyl-D-diphenylalanyl-L-proline using the procedure described in Example 1, Step C and D; yield 48%.

¹H NMR (CD₃OD) δ 1.46 (m, 1H), 1.61 (m, 1H), 1.71 (m, 1H), 1.85 (m, 1H), 2.35 (s, 3H), 2.91 (m, 1H), 3.78 (m, 1H), 4.09 (m, 1H), 4.31–4.39 (m, 2H), 4.45 (m, 1H), 4.91 (m, 1H), 7.18–7.55 (m, 11H), 7.73 (m, 2H).

FAB MS: 563 [M+1]⁺

EXAMPLE 18

Preparation of N-aminosulfonyl-D-diphenylalanyl-L-prolyl-[(4-amidino-3-aminophenyl)methyl]amide.TFA

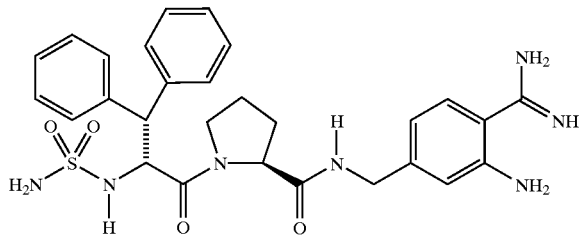

(A) 4-Bromomethyl-2-nitrobenzonitrile

This compound was prepared from 4-methyl-2-nitrobenzonitrile essentially according to the procedure of Example 9, Step B; yield 42%.

$^1$H NMR (CDCl$_3$) δ 8.34 (s, 1H), 7.90 (d, 1H), 7.84 (d, 1H), 4.54 (s, 2H).

FAB MS: 242 [M+1]$^+$

B) 2-Nitro-4-aminomethylbenzonitrile.HCl

This compound was prepared from 4-bromomethyl-2-nitrobenzonitrile essentially according to the procedure of Example 9, Step C; yield 85%.

$^1$H NMR (CD$_3$OD) δ 8.25 (s, 1H), 7.85 (d, 1H), 7.74 (d, 1H), 4.80 (s, 2H).

FAB MS: 178 [M+1]$^+$

C) N-Aminosulfonyl-D-diphenylalanyl-L-prolyl-[(4-cyano-3-nitrophenyl)methyl]amide This compound was prepared from 2-nitro-4-aminomethylbenzonitrile.HCl and N-aminosulfonyl-D-diphenylalanyl-L-proline using the procedure described in Example 1, Step C; yield 70%.

$^1$H NMR (CDCl$_3$) δ 8.19 (s, 1H), 7.76 (d, 1H), 7.68 (d, 1H), 7.38–7.24 (m, 10H), 5.49 (m, 1H), 5.10 (s, 2H), 4.79 (dd, 1H), 4.58 (dd, 1H), 4.39–4.36 (m, 2H), 3.62 (m, 1H), 2.59 (m, 1H), 1.75–1.47 (m, 4H).

FAB MS: 576[M+1]$^+$

D) N-Aminosulfonyl-D-diphenylalanyl-L-prolyl-[(4-cyano-3-aminophenyl)methyl]amide The compound prepared in Step C (0.2 g, 0.35 mmol) was dissolved in methanol (6 mL). To this solution was added 10% palladium-on-carbon (200 mg) and the mixture stirred for 3 h under H$_2$ (20 psi). The reaction mixture was filtered through Celite and the filtrate concentrated in vacuo. The residue was purified by column chromatography (EtOAc:n-hexane, 4:1) to give the title compound (0.17 g, 89%).

$^1$H NMR (CDCl$_3$) δ 7.51 (s, 1H), 7.32–7.20 (m, 10H), 6.91 (d, 1H), 6.80 (d, 1H), 5.39 (m, 1H), 5.05 (s, 2H), 4.89 (dd, 1H), 4.47 (dd, 1H), 4.34–4.25 (m, 2H), 3.51 (m, 1H), 2.49 (m, 1H), 1.65–1.45 (m, 4H).

FAB MS: 546[M+1]$^+$

E) N-Aminosulfonyl-D-diphenylalanyl-L-prolyl-[(4-amidino-3-aminophenyl)methyl]amide.TFA This compound was prepared from the compound obtained in Step D using the procedure described in Example 1, Step D; yield 66%.

$^1$H NMR (CD$_3$OD) δ 7.50 (m, 2H), 7.37 (m, 2H), 7.27–7.17 (m, 7H), 6.84 (d, 1H), 6.76 (d, 1H), 5.05 (s, 2H), 4.33 (d, 1H), 4.31 (s, 2H), 3.69 (m, 1H), 2.92 (m, 1H), 1.79–1.40 (m, 4H).

FAB MS: 564[M+1]$^+$

EXAMPLE 19

Preparation of N-aminosulfonyl-D-diphenylalanyl-L-prolyl-[(4-amidino-3-methoxyphenyl)methyl]amide.TFA

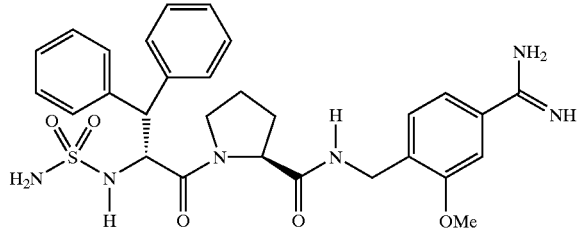

This compound was prepared from N-aminosulfonyl-D-diphenylalanyl-L-proline and 4-aminomethyl-3-methoxybenzonitile.HCl (WO9625426) essentially according to the procedure of Example 1, Step C and D.

$^1$H NMR (CD$_3$OD) δ 1.45 (m, 1H), 1.62 (m, 1H), 1.73 (m, 1H), 1.88 (m, 1H), 2.93 (m, 1H), 3.78–3.85 (m, 4H), 4.12 (m, 1H), 4.28–4.33 (m, 2H), 4.51 (m, 1H), 4.98 (m, 1H), 7.18–7.73 (m, 13H).

FAB MS: 579 [M+1]$^+$

EXAMPLE 20

Preparation of N-aminosulfonyl-D-tyrosinyl-L-prolyl-[(4-amidinophenyl)methyl]amide.TFA

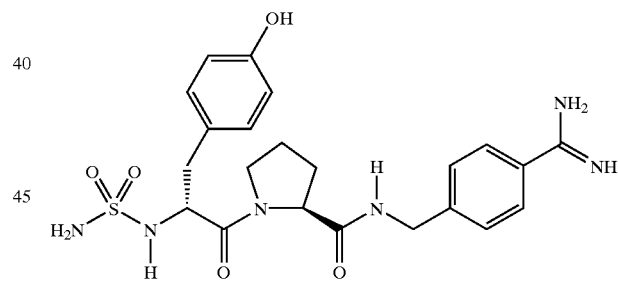

A) N-Aminosulfonyl-D-tyrosinyl-L-proline

This compound was prepared from D-tyrosinyl-L-proline methyl ester according to the procedure of Example 1, Step A and B; yield 69%.

$^1$H NMR (CD$_3$OD) δ 7.58 (d, 2H), 7.49 (d, 2H), 4.41–4.35 (m, 2H), 3.64 (m, 1H), 3.40 (m, 1H), 3.11 (m, 1H), 2.97 (m, 1H), 2.60 (m, 1H), 1.93–1.40 (m, 4H).

FAB MS: 358 [M+1]$^+$

B) N-Aminosulfonyl-D-tyrosinyl-L-prolyl-[(4-cyanophenyl)methyl]amide

This compound was prepared from N-aminosulfonyl-D-tyrosinyl-L-proline according to the procedure of Example 1, Step C; yield 60%.

$^1$H NMR (CD$_3$OD) δ 7.66 (d, 2H), 7.45 (d, 2H), 7.06 (d, 2H), 6.71 (d, 2H) 4.58 (m, 1H), 4.40 (d, 2H), 4.39–4.28 (m,

2H), 3.64 (m, 1H), 2.92–2.87 (m, 2H), 2.72 (m, 1H), 2.00–1.52 (m, 4H).

FAB MS: 472 [M+1]+

C) N-Aminosulfonyl-D-tyrosinyl-L-prolyl-[(4-amidinophenyl)methyl]amide.TFA

This compound was prepared from the compound obtained in Step B according to the procedure of Example 1, Step D; yield 55%.

$^1$H NMR (CD$_3$OD) δ 7.76 (d, 2H), 7.51 (d, 2H), 7.07 (d, 2H), 6.73 (d, 2H) 4.43–4.30 (m, 4H), 3.66 (m, 1H), 2.94–2.85 (m, 2H), 2.73 (m, 1H), 1.90–1.55 (m, 4H).

FAB MS: 489 [M+1]+

EXAMPLE 21

Preparation of N-t-butoxycarbonyl-D-diphenylalanyl-L-prolyl-[(4-amidinophenyl)methyl]amide.TFA

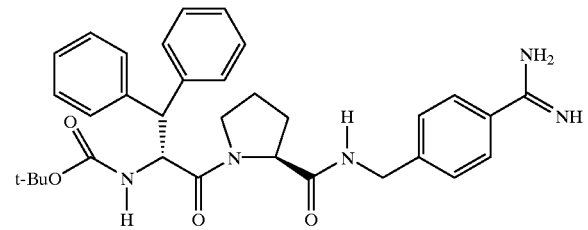

A) N-Boc-D-diphenylalanyl-L-prolyl-[(4-cyanophenyl)methyl]amide

To a solution of N-Boc-D-diphenylalanyl-L-proline (2 g, 4.5 mmol) in DMF (50 mL) was added 4-aminomethylbenzonitrile.HCl (0.84 g, 5 mmol), EDC (1.14 g, 5.9 mmol), HOBT (0.4 g, 5.4 mmol), and triethylamine (2 mL, 14 mmol) and the mixture stirred overnight at rt. The solvent was removed in vacuo and the residue dissolved in EtOAc and washed sequentially with a saturated sodium bicarbonate solution, 1N HCl, and brine. After the solution was dried over magnesium sulfate and concentrated in vacuo, the residue was purified by column chromatography (EtOAc:n-hexane, 2:1) to give the title compound (2.1 g, 84%).

$^1$H NMR (CDCl$_3$) δ 1.35–1.48 (m, 11H), 1.67 (m, 1H), 2.02 (m, 1H), 2.45 (m, 1H), 3.62 (m, 1H), 4.20 (m, 1H), 4.40 (m, 2H), 4.61 (m, 1H), 4.86 (m, 1H), 5.19 (m, 1H), 7.15–7.48 (m, 11H), 7.62 (m, 3H).

FAB MS: 553 [M+1]+

B) N-t-Butoxycarbonyl-D-diphenylalanyl-L-prolyl-[(4-amidinophenyl)methyl]amide.TFA This compound was prepared from the compound obtained in Step A using the procedure described in Example 1, Step D; yield 60%.

$^1$H NMR (CD$_3$OD) δ 1.38–1.65 (m, 11H), 1.84 (m, 2H), 2.80 (m, 1H), 3.75 (m, 1H), 4.12 (m, 1H), 4.42 (m, 2H), 4.57 (m, 1H), 5.08 (m, 1H), 7.15–7.55 (m, 12H), 7.74 (m, 2H).

FAB MS: 570 [M+1]+

EXAMPLE 22

Preparation of N-methoxycarbonyl-D-diphenylalanyl-L-prolyl-[(4-amidinophenyl)methyl]amide.TFA

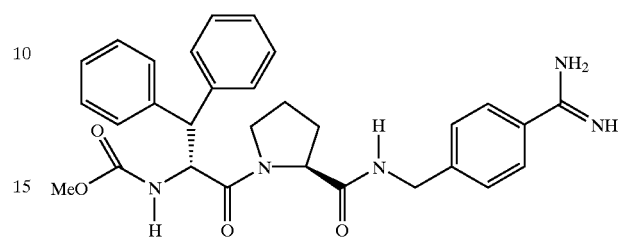

A) N-Methoxycarbonyl-D-diphenylalanyl-L-prolyl-[(4-cyanophenyl)methyl]amide

To a cooled solution of N-Boc-D-diphenylalanyl-L-prolyl-[(4-cyanophenyl)methyl]amide prepared in Example 21, Step A (0.17 g, 0.3 mmol) in methanol (3 mL) was added dropwise acetylchloride (0.3 mL). After stirring for 2 h at rt, the solution was removed to dryness to give D-diphenylalanyl-L-prolyl-[(4-cyanophenyl)methyl]amide.HCl as a white solid (0.15 g, 100%). This was dissolved in dichloromethane (2 mL) and cooled to 0° C. To this was added triethylamine (0.13 mL, 0.92 mmol) and methyl chloroformate (0.04 mL) and the mixture stirred at rt for 2 h. The solution was concentrated and the residue purified by column chromatography (EtOAc:n-hexane, 2:1) to give the title compound (0.13 g, 81%).

$^1$H NMR (CDCl$_3$) δ 1.45 (m, 2H), 1.70 (m, 1H), 2.19 (m, 1H), 2.51 (m, 1H), 3.20 (s, 3H), 3.68 (m, 1H), 4.25 (m, 1H), 4.40 (m, 2H), 4.77 (m, 1), 4.88 (m, 1H), 5.24 (m, 1H), 7.28–7.48 (m, 11H), 7.68 (m, 3H).

FAB MS: 511 [M+1]+

B) N-Methoxycarbonyl-D-diphenylalanyl-L-prolyl-[(4-midinophenyl)methyl]amide.TFA This compound was prepared from the compound obtained in Step A essentially according to the procedure of Example 1, Step D; yield 62%.

$^1$H NMR (CD$_3$OD) δ 1.49 (m, 1H), 1.65 (m, 1H), 1.84 (m, 2H), 2.89 (m, 1H), 3.29 (s, 3H), 3.83 (m, 1H), 4.12 (m, 1H), 4.38 (m, 2H), 4.57 (m, 1H), 5.12 (m, 1H), 7.18–7.52 (m, 12H), 7.83 (m, 2H).

FAB MS: 528 [M+1]+

EXAMPLE 23

Preparation of N-propyloxycarbonyl-D-diphenylalanyl-L-prolyl-[(4-amidinophenyl)methyl]amide.TFA

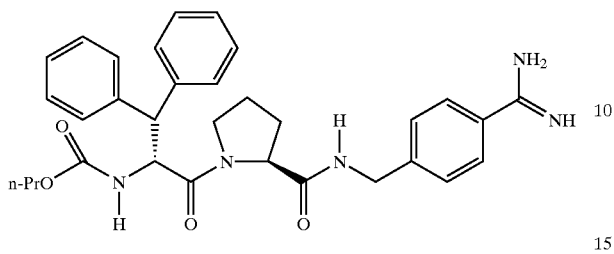

This compound was prepared using the same procedure as described in Example 22 except that propylchloroformate was used instead of methylchloroformate; yield 57%.

$^1$H NMR (CD$_3$OD) δ 0.91 (t, 3H), 1.35–1.51 (m, 3H), 1.67 (m, 1H), 1.88 (m, 2H), 2.85 (m, 1H), 3.35 (s, 3H), 3.89 (m, 1H), 4.02–4.15 (m, 3H), 4.35 (m, 2H), 4.62 (m, 1H), 5.11 (m, 1H), 7.18–7.60 (m, 12H), 7.82 (m, 2H).

FAB MS: 556 [M+1]$^+$

EXAMPLE 24

Preparation of N-benzyloxycarbonyl-D-diphenylalanyl-L-prolyl-[(4-amidinophenyl)methyl]amide.TFA

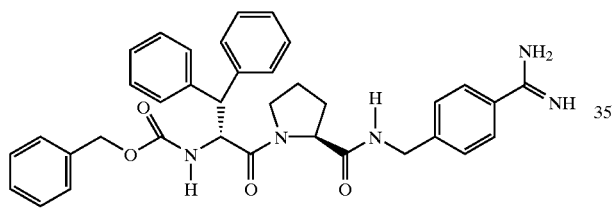

This compound was prepared using the same procedure as described in Example 22 except that benzylchloroformate was used instead of methylchloroformate; yield 41%.

$^1$H NMR (CD$_3$OD) δ 1.53 (m, 1H), 1.71 (m, 1H), 1.89 (m, 2H), 2.81 (m, 1H), 3.25 (s, 3H), 3.85 (m, 1H), 4.22 (m, 1H), 4.38 (m, 2H), 4.51 (m, 1H), 5.07 (m, 3H), 7.15–7.62 (m, 17H), 7.80 (m, 2H).

FAB MS: 604 [M+1]$^+$

EXAMPLE 25

Preparation of N-phenyloxycarbonyl-D-diphenylalanyl-L-prolyl-[(4-amidinophenyl)methyl]amide.TFA

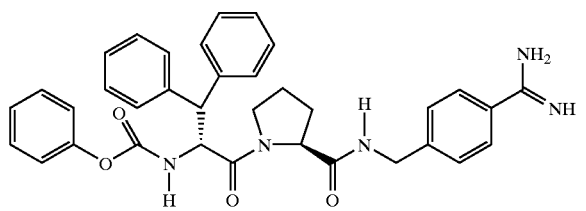

This compound was prepared using the same procedure as described in Example 22 except that phenylchloroformate was used instead of methylchloroformate; yield 63%.

$^1$H NMR (CD$_3$OD) δ 1.51 (m, 1H), 1.60 (m, 1H), 1.73 (m, 1H), 1.88 (m, 1H), 2.93 (m, 1H), 3.31 (s, 3H), 3.88 (m, 1H), 4.17 (m, 1H), 4.29 (m, 1H), 4.43 (m, 1H), 4.57 (m, 1H), 5.12 (m, 1H), 7.10–7.58 (m, 17H), 7.79 (m, 2H).

FAB MS: 590 [M+1]$^+$

EXAMPLE 26

Preparation of N-methoxycarbonyl-D-3,4-dichlorophenylalanyl-L-prolyl-[(4-amidinophenyl)methyl]amide.TFA

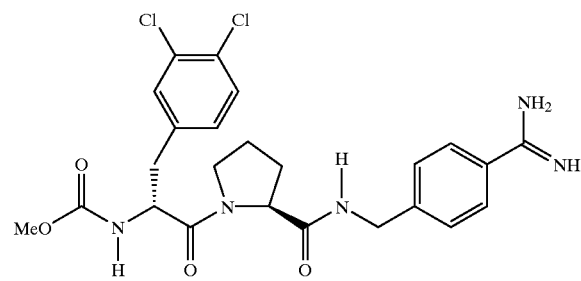

A) N-Butoxycarbonyl-D-3,4-dichlorophenylalanyl-L-proline

This compound was prepared from N-Boc-D-3,4-dichlorophenylalanyl-L-proline using the procedure described in Example 21, Step A; yield 91%.

$^1$H NMR (CD$_3$OD) δ 1.43 (m, 1H), 1.75 (m, 1H), 1.88 (m, 1H), 2.09 (m, 1H), 2.88–3.12 (m, 3H), 3.29 (s, 3H), 3.75 (m, 1H), 4.25–4.55 (m, 4H), 7.15–7.55 (m, 5H), 7.78 (m, 2H).

FAB MS: 504 [M+1]$^+$

B) N-Methoxycarbonyl-D-3,4-dichlorophenylalanyl-L-prolyl-[(4-amidinophenyl)methyl]amide.TFA This compound was prepared from the compound obtained Step A using the procedure described in Example 22, Step A and B; yield 30%.

$^1$H NMR (CD$_3$OD) δ 1.31 (m, 1H), 1.70 (m, 1H), 1.95–2.05 (m, 2H), 2.95 (m, 2H), 3.04 (m, 1H), 3.35 (s, 3H), 3.87 (m, 1H), 4.32–4.58 (m, 4H), 7.18 (m, 1H), 7.40–7.58 (m, 4H), 7.75 (m, 2H).

FAB MS: 521 [M+1]$^+$

EXAMPLE 27

Preparation of N-methoxycarbonyl-D-dicyclohexylalanyl-L-prolyl-[(4-amidinophenyl)methyl]amide.TFA

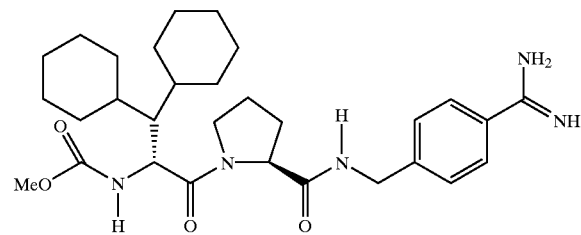

This compound was prepared from N-Boc-D-dicyclohexylalanyl-L-proline using the procedure described in Example 21, Step A and Example 22; yield 21%.

¹H NMR (CD₃OD) δ 1.12–2.20 (m, 27H), 3.27–3.35 (m, 4H), 3.83 (m, 1H), 4.22–4.48 (m, 3H), 5.12 (m, 1H), 7.52 (m, 2H), 7.68 (m, 2H)

FAB MS: 540 [M+1]⁺

EXAMPLE 28

Preparation of N-methoxycarbonyl-D-diphenylalanyl-L-azetidine-2-carboxyl-[(4-amidinophenyl)methyl]amide.TFA

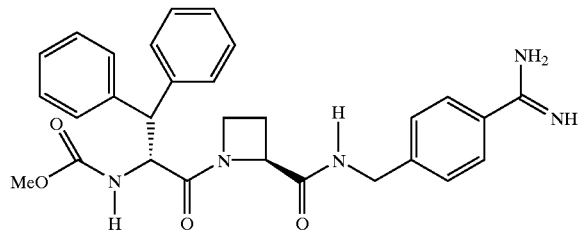

This compound was prepared from N-Boc-D-diphenylalanyl-L-azetidine carboxylic acid using the procedure described in Example 21, Step A and Example 22; yield 33%.

¹H NMR (CD₃OD) δ 2.55 (m, 1H), 2.85 (m, 2H), 3.35 (s, 3H), 3.82 (m, 1H), 3.95 (m, 1H), 4.10 (m, 2H), 4.35 (m, 2H), 4.55 (m, 1H), 4.85 (m, 1H), 7.15–7.50 (m, 12H), 7.73 (m, 2H).

FAB MS: 514 [M+1]⁺

EXAMPLE 29

Preparation of N-methoxycarbonyl-D-cyclohexylglycinyl-L-prolyl-[(4-amidinophenyl)methyl]amide.TFA

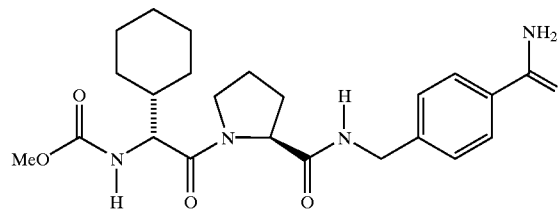

This compound was prepared from N-Boc-D-cyclohexylglycinyl-L-proline using the procedure described in Example 21, Step A and Example 22; yield 25%.

¹H NMR (CD₃OD) δ 0.90–1.91 (m, 14H), 2.11 (m, 1H), 3.19 (m, 1H), 3.35 (s, 3H), 3.88 (m, 1H), 4.32–4.60 (m, 3H), 5.01 (m, 1H), 7.45 (m, 2H), 7.70 (m, 2H).

FAB MS: 444 [M+1]⁺

EXAMPLE 30

Preparation of N-methoxycarbonyl-D-cyclohexylalanyl-L-prolyl-[(4-amidinophenyl)methyl]amide.TFA

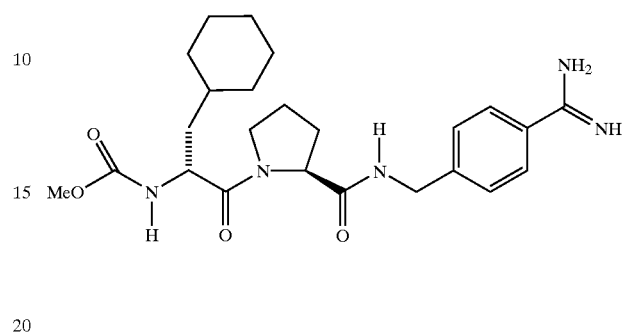

This compound was prepared from N-Boc-D-cyclohexylalanyl-L-proline using the procedure described in Example 21, Step A and Example 22; yield 40%.

¹H NMR (CD₃OD) δ 0.82–1.77 (m, 12H), 1.89–2.18 (m, 5H), 3.29 (s, 3H), 3.42 (m, 1H), 3.91 (m, 1H), 4.25–4.49 m, 3H), 5.01 (m, 1H), 7.45 (m, 2H), 7.72 (m, 2H).

FAB MS: 458 [M+1]⁺

EXAMPLE 31

Preparation of N-methoxycarbonyl-D-diphenylalanyl-L-prolyl-(6-amidino-3-picolyl)amide.TFA

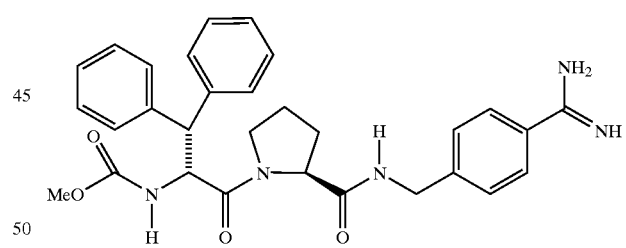

This compound was prepared using the same procedure as described in Example 21, Step A and Example 22 except that 6-cyano-3-picolylamine.HCl was used instead of 4-aminomethylbenzonitrile.HCl.

¹H NMR (CD₃OD) δ 8.78 (s, 1H), 8.10(d, 1H), 7.96 (d, 1H), 7.39 (m, 2H), 7.33 (m, 2H), 7.25 (m, 6H), 5.1 (d, 1H), 4.56 (dd, 1H), 4.45 (dd, 1H), 4.38 (d, 1H), 4.09 (m, 1H), 3.82 (m, 1H), 3.29. (s, 3H), 2.93 (m, 1H), 1.84–1.48 (m, 4H).

FAB MS: 529 [M+1]⁺

EXAMPLE 32

Preparation of N-methoxycarbonyl-D-dicyclohexylalanyl-L-prolyl-(6-amidino-3-picolyl)amide.TFA

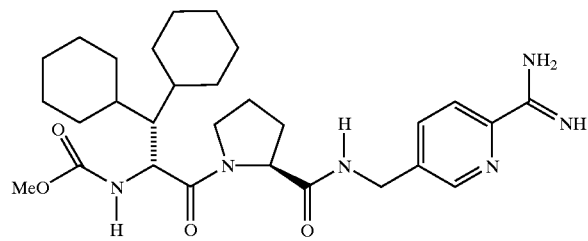

This compound was prepared from N-Boc-D-dicyclohexylalanyl-L-proline and 6-cyano-3-picolylamine.HCl using the procedure described in Example 21, Step A and Example 22; yield 13%.

$^1$H NMR (CD$_3$OD) δ 8.72 (s, 1H), 8.08 (d, 1H), 7.99 (d, 1H), 5.07 (m, 1H), 4.18–4.53 (m, 3H), 3.79 (m, 1H), 3.42 (s, 3H), 3.31 (m, 1H), 2.18–1.07 (m, 27H).

FAB MS: 541 [M+1]$^+$

EXAMPLE 33

Preparation of N-methoxycarbonyl-D-diphenylalanyl-L-prolyl-(5-amidino-2-picolyl)amide.TFA

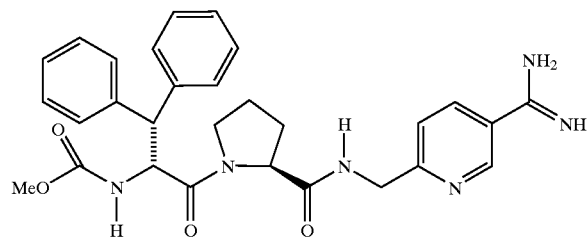

This compound was prepared using the same procedure as described in Example 21, Step A and Example 22 except that 5-cyano-2-picolylamine.HCl prepared in Example 13, Step A was used instead of 4-aminomethylbenzonitrile.HCl.

$^1$H NMR (CD$_3$OD) δ 8.67 (s, 1H), 8.05 (d, 1H), 7.89 (d, 1H), 7.29 (m, 2H), 7.23 (m, 2H), 7.21 (m, 6H), 5.1 (d, 1H), 4.46 (dd, 1H), 4.40 (dd, 1H), 4.28 (d, 1H), 4.02 (m, 1H), 3.72 (m, 1H), 3.31 (s, 3H), 2.90 (m, 1H), 1.79–1.45 (m, 4H).

FAB MS: 529 [M+1]$^+$

EXAMPLE 34

Preparation of N-methoxycarbonyl-D-diphenylalanyl-L-prolyl-[(2-amidino-5-pyrimidyl)methyl]amide.TFA

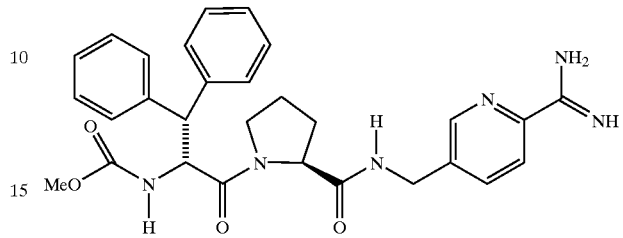

This compound was prepared using the same procedure as described in Example 21, Step A and Example 22 except that 5-aminomethylpyrimidine-2-carbonitrile.HCl (WO9625426) was used instead of 4-aminomethylbenzonitrile.HCl.

$^1$H NMR (CD$_3$OD) δ 8.72(m, 2H), 7.44–7.35(m, 4H), 7.26–7.24 (m, 6H), 4.55(dd, 1H), 4.33–4.30 (m, 2H) 4.06 (dd, 1H), 3.76(m, 1H), 3.28 (s, 3H), 2.90(m, 1H), 1.84–1.45 (m, 4H).

FAB MS: 530 [M+1]$^+$

EXAMPLE 35

Preparation of N-methloxycarbonyl-D-diphenylalanyl-L-prolyl-[(4-amidino-3-fluorophenyl)methyl]amide.TFA

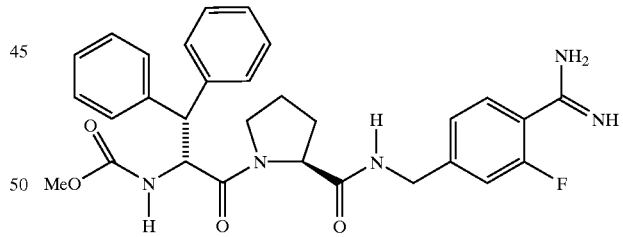

This compound was prepared using the same procedure as described in Example 21, Step A and Example 22 except that 4-cyano-3-fluorobenzylamine.HCl prepared in Example 15, Step C was used instead of 4-aminomethylbenzonitrile.HCl.

$^1$H NMR (CD$_3$OD) δ 1.52 (m, 1H), 1.63 (m, 1H), 1.73–1.88 (m, 2H), 2.92 (m, 1H), 3.45(s, 3H), 3.82 (m, 1H), 4.18 (m, 1H), 4.41 (m, 2H), 4.52 (m, 1H), 5.02 (m, 1H), 7.20–7.51 (m, 12H), 7.62 (m, 1H)

FAB MS: 547 [M+1]$^+$

EXAMPLE 36

Preparation of N-methoxycarbonyl-D-diphenylalanyl-L-prolyl-[(4-amidino-3-methoxyphenyl)methyl]amide.TFA

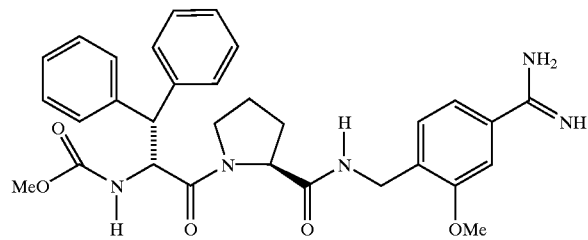

This compound was prepared using the same procedure as described in Example 21, Step A and Example 22 except that 4-aminomethyl-3-methoxybenzonitile.HCl (WO9625426) was used instead of 4-aminomethylbenzonitrile.HCl.

$^1$H NMR (CD$_3$OD) δ 1.51 (m, 1H), 1.63 (m, 1H), 1.72–1.86 (m, 2H), 3.01 (m, 1H), 3.42 (s, 3H), 3.75–3.83 (m, 4H), 4.11 (m, 1H), 4.25–4.36 (m, 2H), 4.52 (m, 1H), 5.03 (m, 1H), 7.20–7.75 (m, 13H)

FAB MS: 558 [M+1]$^+$

EXAMPLE 37

Preparation of N-methoxycarbonyl-D-diphenylalanyl-L-prolyl-[(4-amidino-3-methylphenyl)methyl]amide.TFA

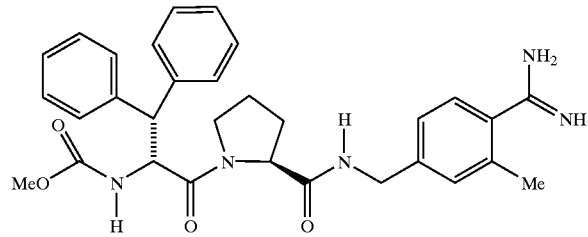

This compound was prepared using the same procedure as described in Example 21, Step A and Example 22 except that 4-cyano-3-methylbenzylamine.HCl prepared in Example 17, Step B was used instead of 4-aminomethylbenzonitrile.HCl.

$^1$H NMR (CD$_3$OD) δ 1.47 (m, 1H), 1.60 (m, 1H), 1.85 (m, 2H), 2.30 (s, 3H), 2.86 (m, 1H), 3.23 (s, 3H), 3.83 (m, 1H), 4.15 (m, 1H), 4.36 (m, 2H), 4.53 (m, 1H), 5.10 (m, 1H), 7.18–7.52 (m, 11H), 7.82 (m, 2H).

FAB MS: 542 [M+1]$^+$

EXAMPLE 38

Preparation of N-acetyl-D-diphenylalanyl-L-prolyl-[(4-amidinophenyl)methyl]amide.TFA

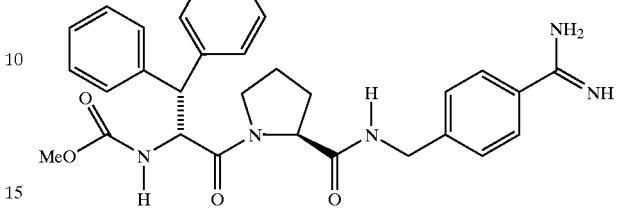

This compound was prepared using the same procedure as described in Example 22 except that acetyl chloride was used instead of methyl chloroformate.

$^1$H NMR (CD$_3$OD) δ 1.51 (m, 1H), 1.68 (m, 1H), 1.87 (m, 2H), 2.15 (s, 3H), 2.92 (m, 1H), 3.84 (m, 1H), 4.5 (m, 1H), 4.42 (m, 2H), 4.61 (m, 1H), 5.12 (m, 1H), 7.18–7.57 (m, 12H), 7.72 (m, 2H).

FAB MS: 512 [M+1]$^+$

EXAMPLE 39

Preparation of D-diphenylalanyl L-prolyl-[(4-amidinophenyl)methyl]amide.2TFA

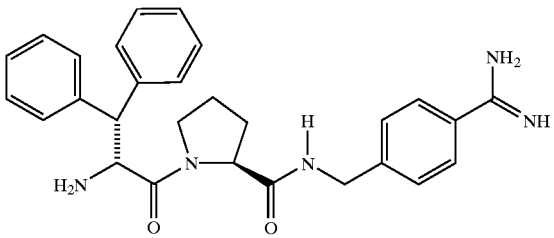

TFA (2 mL) was added to a solution of N-t-butoxycarbonyl-D-diphenylalanyl-L-prolyl-[(4-amidinophenyl)methyl]amide.TFA (Example 21, 208 mg, 0.365 mmol) in dichloromethane (1 mL), and the mixture stirred for 30 min at rt. After the solution was concentrated in vacuo, the residue was purified by preparative HPLC (TFA (0.1%)-H$_2$O—MeOH gradient) to give the title compound (200 mg, 69%).

$^1$H NMR (CD$_3$OD) δ 7.78 (d, 2H), 7.62 (d, 2H), 7.55 (d, 2H), 7.47 (t, 2H), 7.39–7.21 (m, 6H), 5.18 (d, 1H), 4.50 (m, 3H), 4.11 (dd, 1H), 3.62 (m, 1H), 2.81 (m, 1H), 1.77 (m, 3H), 1.31 (m, 1H)

FAB MS: 470 [M+1]$^+$

EXAMPLE 40

Preparation of N-methylsulfonyl-D-diphenylalanyl-L-prolyl-[(4-amidinophenyl)methyl]amide.TFA

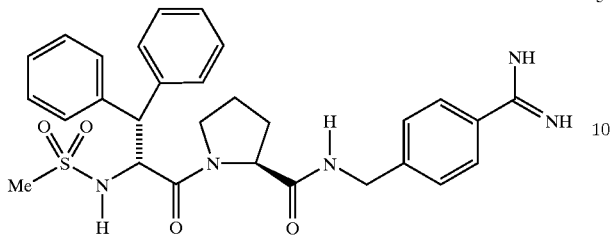

A) N-Methylsulfonyl-D-diphenylalanyl-L-prolyl-[(4-cyanophenyl)methyl]amide

This compound was prepared using the same procedure as described in Example 22, Step A except that methanesulfonylchloride was used instead of methyl chloroformate.

FAB MS: 531 [M+1]$^+$

B) N-Methylsulfonyl-D-diphenylalanyl-L-prolyl-[(4-amidinophenyl)methyl]amide.TFA This compound was prepared from the compound obtained in Step A using the procedure described in Example 1, Step D.

$^1$H NMR (CD$_3$OD) δ 8.24 (m, 1H), 7.76 (m, 2H), 7.52 (m, 4H), 7.48–7.18 (m, 8H), 5.02 (d, 1H), 4.44 (m, 2H), 4.34 (d, 1H), 4.09 (m, 1H), 3.72 (m, 1H), 2.98 (m, 1H), 2.84 (s, 3H), 1.80 (m, 2H), 1.67 (m, 1H), 1.40 (m, 1H),

FAB MS: 548 [M+1]$^+$

EXAMPLE 41

Preparation of N-benzylsulfonyl-D-diphenylalanyl-L-prolyl-[(4-amidinophenyl)methyl]amide.TFA

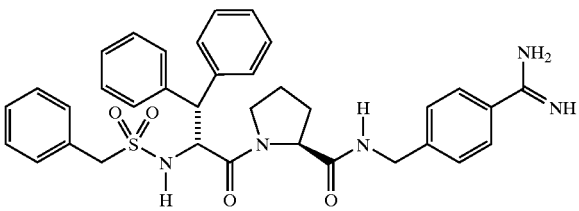

A) N-Benzylsulfonyl-D-diphenylalanyl-L-prolyl-[(4-cyanophenyl)methyl]amide

This compound was prepared using the same procedure as described in Example 22, Step A except that benzylsulfonylchloride was used instead of methyl chloroformate; yield 81%.

$^1$H NMR (CDCl$_3$) δ 7.52–7.42 (m, 6H), 7.38–7.18 (m, 11H), 6.96 (d, 2H), 5.11 (d, 1H), 4.88 (t, 1H), 4.36 (d, 1H), 4.35 (d, 2H), 4.06 (d, 1H), 3.93 (d, 1H), 3.61 (m, 1H), 2.58 (m, 1H), 2.09–1.31 (m, 4H).

FAB MS: 607 [M+1]$^+$

B) N-Benzylsulfonyl-D-diphenylalanyl-L-prolyl-[(4-amidinophenyl)methyl]amide.TFA This compound was prepared from the compound obtained in Step A using the procedure described in Example 1, Step D; yield 82%.

$^1$H NMR (CD$_3$OD) δ 7.65 (m, 2H), 7.48 (m, 4H), 7.40–7.12 (m, 13H), 5.08 (d, 2H), 4.37 (d, 2H), 4.35 (d, 1H), 4.19 (s, 2H), 4.05 (m, 1H), 3.77 (m, 1H), 2.97 (m, 1H), 1.82 (m, 2H), 1.61–1.28 (m, 2H).

FAB MS: 624 [M+1]$^+$

EXAMPLE 42

Preparation of N-dimethylaminosulfonyl-D-diphenylalanyl-L-prolyl-[(4-amidinophenyl)methyl]amide.TFA

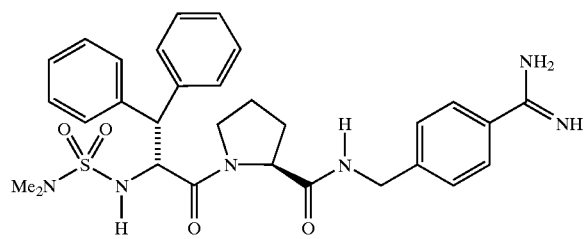

A) N-Dimethylaminosulfonyl-D-diphenylalanyl-L-prolyl-[(4-cyanophenyl)methyl]amide This compound was prepared using the same procedure as described in Example 22, Step A except that dimethylsulfamoylchloride was used instead of methyl chloroformate.

$^1$H NMR (CDCl$_3$) δ 7.53 (d, 2H), 7.36 (m, 8H), 7.24 (m, 4H), 4.94 (d, 1H), 4.66 (t, 1H), 4.48 (dd, 1H), 4.30 (m, 3H), 3.57 (m, 1H), 2.61 (m, 1H), 2.56 (s, 6H), 2.05–1.41 (m, 4H).

FAB MS: 560 [M+1]$^+$

B) N-Dimethylaminosulfonyl-D-diphenylalanyl-L-prolyl-[(4-amidinophenyl)methyl]amide.TFA This compound was prepared from the compound obtained in Step A using the procedure described in Example 1, Step D; yield 75%.

$^1$H NMR (CD$_3$OD) δ 7.97 (m, 1H), 7.72 (d, 2H), 7.51 (m, 4H), 7.37–7.18 (m, 8H), 4.94 (d, 1H), 4.45 (m, 2H), 4.29 (d, 1H), 4.05 (d, 1H), 3.68 (m, 1H), 3.02 (m, 1H), 2.58 (s, 6H), 1.88–1.41 (m, 4H).

FAB MS: 577 [M+1]$^+$

EXAMPLE 43

Preparation of N-dimethoxyphosphoryl-D-diphenylalanyl-L-prolyl-[(4-amidinophenyl)methyl]amide.TFA

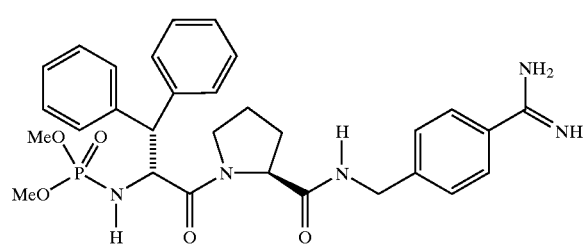

A) N-Dimethoxyphosphoryl-D-diphenylalanyl-L-prolyl-[(4-cyanophenyl)methyl]amide This compound was prepared using the same procedure as described in Example 22, Step A except that dimethyl chlorophosphate was used instead of methyl chloroformate; yield 99%.

¹H NMR (CDCl₃) δ 8.18 (m, 1H), 7.55 (d, 2H), 7.39–7.23 (m, 12H), 4.59 (m, 2H), 4.35 (d,1H), 4.33 (d, 1H), 4.11 (dd, 1H), 3.65 (m,1H), 3.43 (d, 3H), 3.27 (d, 3H), 2.99 (m, 1H), 2.57(m, 1H), 2.06 (m, 1H), 1.45 (m, 2H).

FAB MS: 561 [M+1]⁺

B) N-Dimethoxyphosphoryl-D-diphenylalanyl-L-prolyl-[(4-amidinophenyl)methyl]amide.TFA This compound was prepared from the compound obtained in Step A using the procedure described in Example 1, Step D; yield 75%.

¹H NMR (CD₃OD) δ 7.74 (d, 2H), 7.51–7.25 (m, 12H), 5.02 (d, 1H), 4.78 (dd, 1H), 4.44 (q, 2H), 4.32 (d, 1H), 4.07 (dd, 1H), 3.75 (m, 1H), 3.38 (d, 3H), 3.28 (d, 3H), 3.01 (m, 1H), 1.89–1.48 (m, 4H).

FAB MS: 578 [M+1]⁺

EXAMPLE 44

Preparation of N-dimethylphosphoryl-D-diphenylalanyl-L-prolyl-[(4-amidinophenyl)methyl]amide.TFA

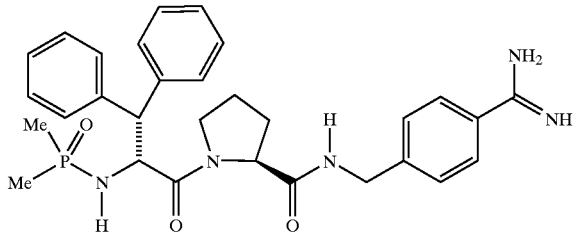

This compound was prepared using the same procedure as described in Example 22 except that dimethylphophinic chloride was used instead of methyl chloroformate.

¹H NMR (CD₃OD) δ 7.75 (d, 2H), 7.53–7.19 (m, 12 H), 4.85 (dd, 4H), 4.59 (d, 1H), 4.31 (s, 2H), 4.09 (dd, 1H), 3.86 (m, 1H), 3.08 (m, 1H), 1.83–1.52 (m, 4H), 1.41 (d, 3H), 1.14 (d, 3H).

FAB MS: 529 [M+1]⁺

EXAMPLE 45

Preparation of N-carboxymethyl-D-diphenylalanyl-L-prolyl-[(4-amidinophenyl)methyl]amide.2TFA

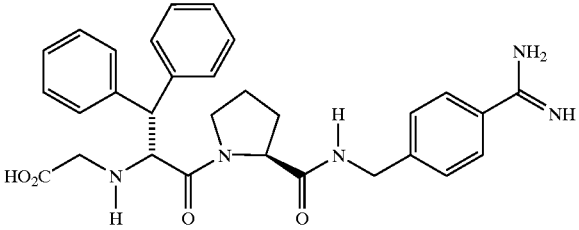

A) N-(t-Butoxycarbonyl)methyl-D-diphenylalanyl-L-prolyl-[(4-cyanophenyl) methyl]amide To a cooled (0° C.) solution of D-diphenylalanyl-L-prolyl-[(4-cyanophenyl)methyl]amide.HCl prepared in Example 22, Step A (400 mg, 0.818 mmol) in acetonitrile (10 mL) was added diisopropylethylamine (0.58 mL, 3.27 mmol) and t-butyl bromoacetate (0.16 mL, 1.06 mmol), and the mixture stirred for 1 day at rt. After the reaction mixture was concentrated in vacuo, the residue was purified by column chromatography (EtOAc:n-hexane, 6:4) to give the title compound (445 mg, 96%).

¹H NMR (CDCl₃) δ 8.01 (m, 1H), 7.57 (d, 2H), 7.37 (m, 6H), 7.28–7.13 (m, 6H), 4.52 (dd, 1H), 4.41(dd, 1H), 4.28 (dd, 2H), 4.14 (d, 1H), 3.27 (m, 1H), 3.21 (dd, 2H), 2.69 (m, 1H), 2.12 (m, 2H), 1.67 (m, 1H), 1.43 (m, 1H), 1.37 (s, 9H).

FAB MS: 567 [M+1]⁺

B) N-(t-Butoxycarbonyl)methyl-D-diphenylalanyl-L-prolyl-[(4-hydroxyamidinophenyl)methyl]amide To a solution of the compound obtained in Step A (100 mg, 0.176 mmol) in ethanol (6 mL) was added hydroxylamine hydrochloride (24.5 mg, 0.352 mmol) and sodium carbonate (40 mg, 0.352 mmol), and the mixture heated at 60° C. for 10 h. After the reaction mixture was concentrated in vacuo, the residue was diluted with EtOAc, washed with brine, dried over magnesium sulfate, and purified by column chromatography (methanol: dichloromethane, 2:23) to give the title compound (95 mg, 90%).

FAB MS: 600 [M+1]⁺

C) N-(t-Butoxycarbonyl)methyl-D-diphenylalanyl-L-prolyl-[(4-hydroxyamidinophenyl)methyl]amide.2AcOH The compound (95 mg, 0.159 mmol) obtained in Step B was dissolved in methanol (5 mL). To this solution was added 10% palladium-on-carbon (20 mg), acetic anhydride (0.03 mL, 0.31 mmol) and the mixture was stirred for 24 h under H₂ (20 psi). The reaction mixture was filtered through Celite and the filtrate was concentrated in vacuo. The residue was purified by preparative HPLC (H₂O—MeOH gradient) to give the title compound (81 mg, 90%).

¹H NMR (CD₃OD) δ 7.76 (d, 2H), 7.55 (d, 2H), 7.50 (d, 2H), 7.37 (t, 2H), 7.26–7.16 (m, 6H), 4.50 (m, 3H), 4.22(d, 1H), 4.08 (dd, 1H), 3.53 (m, 1H), 3.34 (s, 2H), 2.98 (m, 1H), 2.15 (s, 6H), 2.02–1.70 (m, 3H), 1.41 (s, 9H), 1.40(m, 1H).

FAB MS: 584 [M+1]⁺

D) N-Carboxymethyl-D-diphenylalanyl-L-prolyl-[(4-amidinophenyl)methyl]amide.2TFA To a cooled (0° C.) solution of N-(t-butoxycarbonyl)methyl-D-diphenylalanyl-L-prolyl-[(4-cyanophenyl)methyl]amide.2AcOH (120 mg, 0.17 mmol) in dichloromethane (2.5 mL) was added TFA (2.5 mL) and the mixture stirred for 3.5 h. After the reaction mixture was concentrated in vacuo, the residue was purified by preparative HPLC (TFA (0.1%)-H₂O-MeOH gradient) to give the title compound (102 mg, 80%).

¹H NMR (CD₃OD) δ 7.77 (d, 2H), 7.67 (d, 2H), 7.57 (d, 2H), 7.51 (t, 2H), 7.41–7.26 (m, 6H), 5.33 (d, 2H), 4.52 (dd, 2H), 4.10 (dd, 1H), 3.83 (dd, 2H), 3.49 (m, 1H), 2.87 (m, 1H), 1.91–1.72 (m, 3H), 1.30 (m, 1H).

FAB MS: 528 [M+1]⁺

EXAMPLE 46

Preparation of N-carboxymethyl-D-diphenylalanyl-L-prolyl-(6-amidino-3-picolyl)amide.2TFA

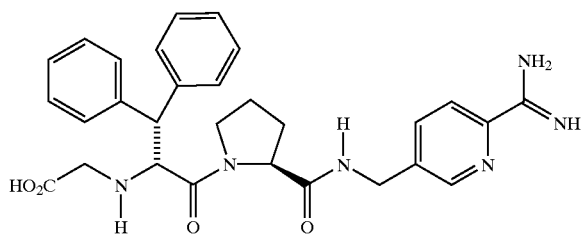

This compound was prepared from D-diphenylalanyl-L-prolyl-(6-cyano-3-picolyl)amide, an intermediate obtained in Example 31, using the procedure described in Example 45.

$^1$H NMR (CD$_3$OD) δ 8.69 (s, 1H), 8.10 (d, 1H), 8.02 (d, 1H), 7.60–7.18 (m, 10H), 5.30 (d, 1H), 4.60 (m, 1H), 4.45 (m, 2H), 4.07 (m, 1H), 3.81–3.73 (dd, 2H), 3.32 (m, 1H), 2.98 (m, 1H), 1.89–1.69 (m, 3H), 1.62 (m, 1H).

FAB MS: 529 [M+1]$^+$

EXAMPLE 47

Preparation of N-carboxymethyl-D-diphenylalanyl-L-prolyl-[(4-amidino-3-fluorophenyl)methyl]amide.2TFA

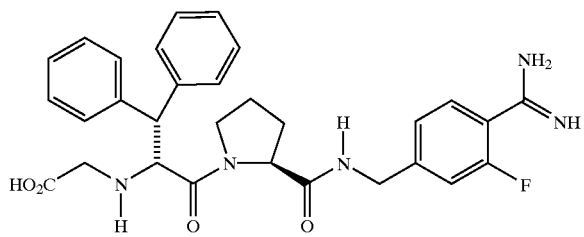

This compound was prepared from D-diphenylalanyl-L-prolyl-[(4-cyano-3-fluorophenyl)methyl]amide, an intermediate obtained in Example 35, using the procedure described in Example 45.

$^1$H NMR (CD$_3$OD) δ 7.67 (m, 1H), 7.59–7.20 (m, 12H), 5.28 (d, 1H), 4.53 (m, 1H), 4.38 (m, 2H), 4.05 (m, 1H), 3.87–3.65 (m, 3H), 2.98 (m, 1H), 1.89–1.78 (m, 2H), 1.62 (m, 1H), 1.53 (m, 1H).

FAB MS: 546 [M+1]$^+$

EXAMPLE 48

Preparation of N-carboxymethyl-D-diphenylalanyl-L-prolyl-[(4-amidino-3-methylphenyl)methyl]amide.2TFA

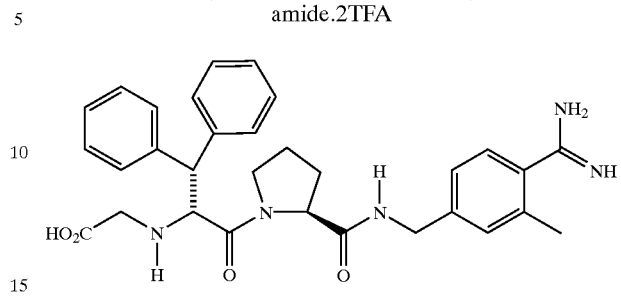

This compound was prepared from D-diphenylalanyl-L-prolyl-[(4-cyano-3-methylphenyl)methyl]amide, an intermediate obtained in Example 37, using the procedure described in Example 45.

$^1$H NMR (CD$_3$OD) δ 7.69 (m, 1H), 7.60 (m, 2H), 7.51–7.13 (m, 10H), 5.35 (d, 1H), 4.49 (m, 1H), 4.35–4.29 (m, 2H), 4.07 (m, 1H), 3.77 (dd, 2H), 3.65 (m, 1H), 3.02 (m, 1H), 2.30 (s, 3H), 2.01–1.85 (m, 2H), 1.65 (m, 1H), 1.50 (m, 1H).

FAB MS: 542 [M+1]$^+$

EXAMPLE 49

Preparation of N-(ethoxycarbonyl)methyl-D-diphenylalanyl-L-prolyl-[(4-hydroxyamidinophenyl)methyl]amide.TFA

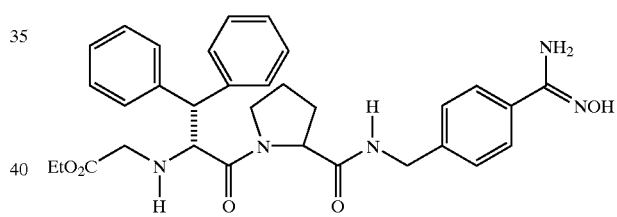

A) N-(Ethoxycarbonyl)methyl-D-diphenylalanyl-L-prolyl-[(4-cyanophenyl)methyl]amide This compound was prepared using the same procedure as described in Example 45, Step A except that ethyl bromoacetate was used instead of t-butyl bromoacetate.

$^1$H NMR (CDCl$_3$) δ 7.60 (m, 2H), 7.35–7.10 (m, 12H), 5.02 (d, 1H), 4.50 (d, 1H), 4.38 (m, 1H), 4.31 (dd, 2H), 4.14 (q, 2H), 3.89 (m, 1H), 3.25 (dd, 2H), 2.78 (m, 1H), 2.08 (m, 2H), 1.72 (m, 1H), 1.50 (m, 1H), 1.21 (t, 3H).

FAB MS: 539 [M+1]$^+$

B) N-(Ethoxycarbonyl)methyl-D-diphenylalanyl-L-prolyl-[(4-hydroxyamidinophenyl)methyl]amide.TFA This compound was prepared from the compound obtained in Step A using the same procedure as described in Example 45, Step B.

$^1$H NMR (CD$_3$OD) δ 7.56 (m, 4H), 7.45 (m, 2H), 7.39 (m, 2H), 7.29–7.16 (m, 6H), 5.07 (d, 1H), 4.45–4.33 (m, 3H), 4.12 (q, 2H), 4.00 (m, 1H), 3.73–3.60 (dd, 2H), 3.38 (m, 1H), 2.80 (m, 1H), 1.68 (m, 3H), 1.17 (m, 1H), 1.14 (t, 3H).

FAB MS: 572 [M+1]$^+$

EXAMPLE 50

Preparation of N-phenyl-D-diphenylalanyl-L-prolyl-[(4-amidinophenyl)methyl]amide.TFA

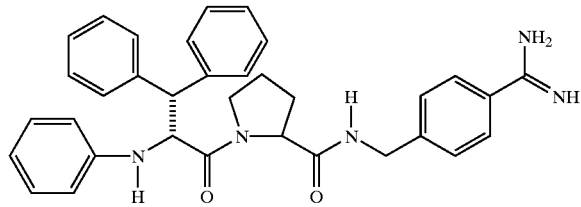

A) N-Phenyl-D-diphenylalanine

To a solution of D-diphenylalanine.HCl (0.5 g, 1.3 mmol) in DMF (3.6 mL) were added iodobenzene (0.16 mL, 1.43 mmol), Pd(PPh$_3$)$_4$ (72 mg, 0.062 mmol), CuI (12.2 mg, 0.064 mmol), K$_2$CO$_3$ (0.18 g, 1.3 mmol), triethylbenzylammonium chloride (44 mg, 0.19 mmol), triethylamine (0.36 mL, 2.58 mmol), and water (0.36 mL), and the mixture was stirred for 4 h at 100° C. The resulting solution was basified to pH 10 with 1N NaOH solution and washed with ethyl acetate (20 mL). The water layer was acidified to pH 2 with 1N HCl and extracted with ethyl acetate (20 mL×2). The combined extracts were dried over magnesium sulfate and concentrated in vacuo to give the title compound (0.21 g, 86%).

$^1$H NMR (CD$_3$OD) δ 7.51–7.15 (m, 11H), 7.07 (m, 2H), 6.60 (m, 2H), 4.74 (d, 1H), 4.42 (d, 1H).

FAB MS: 318 [M+1]$^+$

B) N-Phenyl-D-diphenylalanine-L-proline methyl ester

This compound was prepared from the compound obtained Step A and L-proline methyl ester using the amide-coupling procedure described in Example 1, Step C; yield 36%.

$^1$H NMR (CDCl$_3$) δ 7.47–7.03 (m, 13H), 6.73 (t, 1H), 6.58 (m, 2H), 4.76 (dd, 1H), 4.44 (d, 1H), 4.19 (t, 1H), 4.07 (m, 1H), 3.55 (m, 1H), 3.48 (s, 3H), 2.83 (m, 1H) 1.73 (m, 3H), 1.27 (m, 1H).

FAB MS: [M+1]$^+$ 429

C) N-Phenyl-D-diphenylalanine-L-proline

This compound was prepared from the compound obtained Step B using the standard hydrolysis procedure described in Example 1, Step B; yield 97%.

$^1$H NMR (CD$_3$OD) δ 7.51–7.10 (m, 12H), 6.71 (m, 1H), 6.60 (m, 2H), 4.77 (m, 1H), 4.40 (m, 1H), 4.22 (m, 1H), 4.02 (m, 1H), 3.50 (m, 1H), 2.80 (m, 1H), 1.83 (m, 3H), 1.30 (m, 1H)

FAB MS: 415 [M+1]$^+$

D) N-phenyl-D-diphenylalanyl-L-prolyl-[(4-cyanophenyl)methyl]amide

This compound was prepared from the compound obtained Step C using the procedure described in Example 1, Step C; yield 52%.

$^1$H NMR (CDCl$_3$) δ 7.50–6.99 (m, 13H), 6.95 (m, 1H), 6.69 (m, 1H), 6.53 (m, 2H), 4.87 (m, 1H), 4.55 (d, 1H), 4.44 (d, 1H), 4.19 (dd, 1H), 4.16 (m, 1H), 4.01 (dd, 1H), 3.50 (m, 1H), 2.72 (m, 1H), 2.16 (m, 1H), 1.74 (m, 1H), 1.38 (m, 2H)

FAB MS: 529 [M+1]$^+$

E) N-Phenyl-D-diphenylalanyl-L-prolyl-[(4-amidinophenyl)methyl]amide.TFA

This compound was prepared from the compound obtained Step D using the procedure described in Example 1, Step D; yield 53%.

$^1$H NMR (CD$_3$OD) δ 7.59 (m, 2H), 7.51–7.25 (m, 12H), 7.02 (m, 2H), 6.75–6.63 (m, 3H), 5.06 (m, 1H), 4.43 (m, 1H), 4.25 (m, 2H), 4.12 (m, 1H), 3.66 (m, 1H), 3.07 (m, 1H), 1.93–1.57 (m, 3H), 1.35 (m, 1H)

FAB MS: 546 [M+1]$^+$

EXAMPLE 51

In Vitro Enzyme Assays for Determining Inhibition Constants

The activity of thrombin was measured spectrophotometrically using tosyl-Gly-Pro-Arg-p-nitroanilide acetate (Chromozym TH, Boehringer Mannheim) as a substrate. Thrombin used in this test was prepared from human plasma according to the protocol of Ngai and Chang (see, *Biochem. J.* 1991, 280, 805). Each compound was dissolved in DMSO to make a 1 mM stock solution and dilutions were made thereof with assay buffer (0.1 M TrisHCl, 0.15 M NaCl, 0.1% polyethylene glycol 8000, pH 7.8). Different concentrations of inhibitor were mixed with 0.3 NIH units of thrombin in 0.8 mL of the buffer. The mixture was incubated for 10 min at room temperature before adding 0.2 mL of the substrate to a final concentration of 20 μM. The release of p-nitroaniline by hydrolysis of the substrate was monitored for 5 min by measuring the increase in optical density at 381 nm with a UV2100S spectrometer (Shimadzu). A graph for the reciprocal value of initial velocity to the inhibitor concentration was derived from progress curves by fitting the data using a linear regression program. The inhibition constants (Ki values) were then obtained from the Dixon plot equation (see, *Biochem. J.* 1953, 55, 170). Under these conditions, the Km value for the substrate hydrolysis was 5.2 μM as determined from a non-linear regression analysis of initial rate assuming Michaelis-Menten kinetics.

In certain studies with highly potent inhibitors (Ki<0.1 nM) where the degree of thrombin inhibition was very high, a more sensitive assay was employed. In this assay, the concentration of Chromozym TH and thrombin was set to 80 μM and 1.5 mU/mL, respectively, and the hydrolysis reaction was monitored for 1.5 hr.

Table 1 shows the thrombin inhibitory activity (Ki values) obtained with the exemplary compounds of the present invention. It can be identified that the compounds of the present invention show excellent inhibitory activity against thrombin.

EXAMPLE 52

Pharmacokinetic Studies for Determining Oral Bioavailability

Male Sprague-Dawley rats (250–300 g) were restrained individually in a surgical plate (Dae Jong Instrument Company, Seoul, Korea) as supine position. The femoral artery and the femoral vein (iv only) of rats were cannulated with polyethylene tubing (PE-50, Clay Adams, Parsippany, N.J., USA) under light ether anesthesia. After complete recovery from anesthesia, rats were given 30 mg/kg of test compound dissolved in distilled water via oral gavage or given 10 mg/kg via the femoral vein for intravenous (iv) study. Blood samples (0.25 mL) were collected from the femoral artery at 0 (for control), 1 (iv only), 5, 15, 30, 60, 90 (iv only), 120, 180, and 240 min after dosing.

Male beagle dogs (7–10 kg, Hazleton Research Product Inc., Calamazoo, Mich., USA) were housed individually in a metabolic cage for plasma disposition study. Dogs were orally administered with 10 mg/kg of test compound dissolved in distilled water via gavage or injected with 2 mg/0.2 mL/kg via the cephalic vein using INTROCAN®. Blood samples were withdrawn via the cephalic vein at 0 (for control), 1, 5 (iv only), 15, 30, 60, 90, 120, 180, 240, 360 (po only) and 480 (po only) min after dosing.

Blood samples were taken into heparinized tube (25 U/mL), deproteinized with 2 volumes of methanol, and centrifuged. The resulting supernatant (60 µL) was analyzed by HPLC eluting with a mixture of 0.1% trifluoroacetic acid aqueous solution and acetonitrile with a ratio of 81% to 19%. Plasma concentration of test compound was recorded and used to calculate the pharmacokinetic parameters: maximum plasma concentration of test compound ($C_{max}$), time of maximum plasma concentration ($T_{max}$), area under the curve (AUC), and fraction of test compound absorbed (F).

EXAMPLE 53

In Vivo Studies of the Compounds Claimed Herein were Conducted Using the Following Procedure Male Sprague-Dawley rats (body weights 250–300 g, 3–4/group) were anaesthetized by intraperitoneal injection with urethane solution (1.25 g/kg). The abdomen was surgically opened by a midline incision and the inferior venae cava was carefully dissected free from surrounding connective tissue. The venae iliolumbar and spermatica were ligated with a silk thread. Thrombus formation was initiated by infusion of a thromboplastin preparation (Simplastin®) using an infusion pump (Model 100, IITC Life Science, USA) via the left femoral vein at 0.5 mL/kg/min. Simplastine® (Organon Teknika, USA) was reconstituted with 4 mL of distilled water and then given diluted at 1:2.5 in distilled water. At the start of infusion for 30 seconds, the vena cava was ligatured below the left renal vein. After the end of infusion, vena cava was also ligatured above the iliac veins 16 mm apart from upper ligature. After 15 min of stasis, the thrombus formed inside the vessel was carefully removed and weighed. Before weighing, the excess blood was removed by blotting the wet clot on the wet Whatman filter paper (see, Millet, J.; Theveniaux, J.; Brown, N. L. *Thromb. Haemost.* 1992, 67, 176).

Saline (control) or test compounds (1 mg/kg) were injected as a bolus via the femoral vein starting 5 min before the thromboplastin infusion. Bolus injection volume was 0.5 mL/kg. Antithrombotic activity was expressed as a percentage where:

Antithrombotic activity (%)=100×(A−B)/A

A=mean clot weight of control group

B=mean clot weight of test compound group

The results shows that the compounds of the present invention are effective in preventing thrombotic occlusions.

As shown in Table 1, the di-substituted alanine compounds of the present invention demonstrate significantly higher thrombin affinity compared to the corresponding mono-substituted alanine analogs. In addition, the diphenylalnine compounds of this invention exhibit generally good oral absorption in rats and dogs. In particular, the compounds of this invention possessing both diphenylalaine and amidine exhibit excellent antithrombotic activity (95–100%) in the rat venous thrombosis model.

All the documents cited herein, including the foreign priority documents, are hereby incorporated by reference.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not be the above description, but by the following claims and their equivalents.

TABLE 1

Thrombin inhibition constants of the compounds of the present invention

| Compound No. | Inhibition constant Ki (nM) |
| --- | --- |
| 1 | 0.018 |
| 2 | 4.2 |
| 3 | 0.16 |
| 4 | 0.029 |
| 5 | 0.035 |
| 6 | 0.38 |
| 7 | 0.66 |
| 8 | 43 |
| 9 | 0.027 |
| 10 | 4.2 |
| 11 | 0.046 |
| 12 | 2.1 |
| 13 | 0.055 |
| 14 | 0.023 |
| 15 | 0.030 |
| 16 | 0.016 |
| 17 | 0.32 |
| 18 | 0.20 |
| 19 | 0.060 |
| 20 | 0.39 |
| 21 | 0.080 |
| 22 | 0.030 |
| 23 | 0.035 |
| 24 | 0.040 |
| 25 | 0.150 |
| 26 | 0.47 |
| 27 | 0.020 |
| 28 | 0.060 |
| 29 | 0.52 |
| 30 | 0.91 |
| 31 | 0.015 |
| 32 | 0.020 |
| 33 | 0.040 |
| 34 | 0.040 |
| 35 | 0.050 |
| 36 | 0.090 |
| 37 | 0.44 |
| 38 | 0.26 |
| 39 | 0.036 |
| 40 | 0.005 |
| 41 | 0.01 |
| 42 | 0.002 |
| 43 | 0.011 |
| 44 | 0.15 |
| 45 | 0.02 |
| 46 | 0.03 |
| 47 | 0.05 |
| 48 | 0.22 |
| 49 | 15.7 |
| 50 | 0.045 |

What is claimed is:

1. A compound having formula (I)

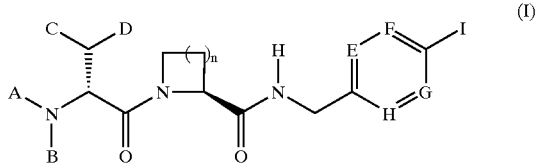

and pharmaceutically acceptable salts thereof
wherein
n is 1 or 2;
A is hydrogen, $C_{1-6}$ alkyl, aryl, —$SO_2R^1$, —$PO(OC_{1-6}$ alkyl$)_2$, —$PO(C_{1-6}$ alkyl$)_2$, —$CO(C_{1-6}$ alkyl), —$CO_2R^2$, or —$(CH_2)_mCO_2(C_{1-6}$ alkyl),
wherein
$R^1$ is hydrogen, $C_{1-6}$ alkyl, $C_{3-7}$ cycloalkyl, aryl, —$(CH_2)_m$aryl or —$NR^3R^4$
$R^2$ is $C_{1-6}$ alkyl, $C_{3-7}$ cycloalkyl, aryl, —$(CH_2)_m$aryl or alkenyl, and
m is 1, 2 or 3,
wherein
aryl is unsubsituted, substituted phenyl or 5–6 membered aromatic heterocyclic ring, and
$R^3$ and $R^4$ are independently hydrogen, $C_{1-6}$ alkyl or $C_{3-7}$ cycloalkyl;
B is hydrogen;
C and D are both
phenyl unsubsituted or substituted with one or two substituents selected from $C_{1-4}$ alkyl, $C_{1-4}$ alkoxy, methylenedioxy, halogen, hydroxy and $NR^4R^5$, or $C_{3-7}$ cycloalkyl;
E, F, and H are independently $CR^5$ or N and G is N,
wherein
$R^5$ is hydrogen, $C_{1-4}$ alkyl, $C_{1-4}$ alkoxy, $CF_3$, halogen, hydroxy or —$NR^3R^4$; and
I is —$C(NH)NH_2$, —$C(NH_2)NOH$, or —$CH_2NH_2$.

2. The compound according to claim 1, wherein C and D are both selected from the group consisting of phenyl and cyclohexyl.

3. The compound according to claim 1, wherein I is —$C(NH)NH_2$.

4. The compound according to claim 1, wherein I is —$C(NH_2)NOH$.

5. The compound according to claim 1, wherein I is $CH_2NH_2$.

6. The compound according to claim 1, wherein the compound is selected from the group consisting of
N-aminosulfonyl-D-diphenylalanyl-L-prolyl-(6-amidino-3-picolyl)amide,
N-aminosulfonyl-D-diphenylalanyl-L-prolyl-(6-aminomethyl-3-picolyl)amide,
N-aminosulfonyl-D-dicyclohexylalanyl-L-prolyl-(6-amidino-3-picolyl) amide,
N-aminosulfonyl-D-diphenylalanyl-L-prolyl-(5-amidino-2-picolyl)amide,
N-aminosulfonyl-D-diphenylalanyl-L-prolyl-[(2-amidino-5-pyrimidyl)methyl]amide,
N-methoxycarbonyl-D-diphenylalanyl-L-prolyl-(6-amidino-3-picolyl) amide,
N-methoxycarbonyl-D-dicyclohexylalanyl-L-prolyl-(6-amidino-3-picolyl) amide,
N-methoxycarbonyl-D-diphenylalanyl-L-prolyl-(5-amidino-2-picolyl) amide, and
N-methoxycarbonyl-D-diphenylalanyl-L-prolyl-[(2-amidino-5-pyrimidyl)methyl]amide.

7. A method of inhibiting serine proteases comprising administering to a mammal in need thereof an effective amount of the compound of claim 1.

8. A method of inhibiting thrombin comprising administering to a mammal in need thereof an effective amount of the compound of claim 1.

* * * * *